US009332770B2

(12) United States Patent
Griffin et al.

(10) Patent No.: US 9,332,770 B2
(45) Date of Patent: May 10, 2016

(54) ANTI-LISTERIAL MIXED CULTURE AND METHOD FOR PRODUCING CHEESE

(75) Inventors: Carmel Griffin, Bandon (IE); Susan Mills, Tralee (IE); Paul Ross, Kilworth (IE); Willem Cornelis Meijer, Ede (NL); Lourdes Mariela Serrano Davalos, Arnhem (NL)

(73) Assignee: CSK Food Enrichment B.V., Leeuwarden (NL)

( * ) Notice: Subject to any disclaimer, the term of this patent is extended or adjusted under 35 U.S.C. 154(b) by 230 days.

(21) Appl. No.: 13/541,416

(22) Filed: Jul. 3, 2012

(65) Prior Publication Data

US 2013/0011516 A1 Jan. 10, 2013

(30) Foreign Application Priority Data

Jul. 4, 2011 (EP) .................................... 11172596

(51) Int. Cl.

| A23C 9/123 | (2006.01) |
| A23C 19/00 | (2006.01) |
| A23C 21/00 | (2006.01) |
| A23C 17/00 | (2006.01) |
| A23C 9/12 | (2006.01) |
| A23C 1/00 | (2006.01) |
| A23C 9/00 | (2006.01) |
| A23B 7/005 | (2006.01) |
| C12N 1/20 | (2006.01) |
| A23C 19/032 | (2006.01) |
| A23L 1/30 | (2006.01) |
| A23C 19/11 | (2006.01) |
| C12R 1/25 | (2006.01) |
| A23L 3/3463 | (2006.01) |

(52) U.S. Cl.
CPC ............. *A23C 19/0323* (2013.01); *A23C 19/11* (2013.01); *A23L 1/3014* (2013.01); *A23L 3/34635* (2013.01); *C12N 1/20* (2013.01); *C12R 1/25* (2013.01); *A23Y 2220/23* (2013.01); *A23Y 2220/67* (2013.01)

(58) Field of Classification Search
CPC ...... A23C 19/0323; A23C 19/11; C12R 1/25; A23L 3/34635; A23L 1/3014; C12N 1/20; A23Y 2220/23; A23Y 2220/63
USPC ....................... 426/36, 491, 43, 41, 401, 399; 435/252.4, 252.9
See application file for complete search history.

(56) References Cited

U.S. PATENT DOCUMENTS

2004/0265289 A1 12/2004 Elsser et al.

FOREIGN PATENT DOCUMENTS

EP 1 273 237 A1 8/2003

OTHER PUBLICATIONS

Nascimento et al., "Applicability of bacteriocin-producing Lactobacillus plantarum, Enterococcus faecium and *Lactococcus lactis* ssp. lactis as adjunct starter in Minas Frescal cheesemaking".

*International Journal of Diary Technology* vol. 61, No. 4 (Nov. 2008).*
Cotter et al., "Bacterial Lantibiotics—Strategies to Improve Therapeutic Potential". Current Protein and Peptide Science, 2005, 6, 61-75.*
"A Guide to Bacteria Preservation: Rerfrigeration, Freezing and Freeze Drying". Available online at www.opsdiagnostics.com on Apr. 30, 2010.*
Fimland et al., "Pediocin-like antimicrobial peptides class IIa bacteriocins and their immunity proteins—biosynthesis structure and mode of action". J Peptide Science 11, 688-696 (2005).*
Extended European Search Report for EP 11172596.6—dated Jan. 5, 2012.
Hanlin, Mary Beth et al: "Bacteriocins of Lactic Acid Bacteria in Combination Have Greater Antibacterial Activity", Journal of Food Protection, International Association for Food Protection, US, vol. 56, No. 3, Jan. 1, 1993, pp. 252-255, XP009154982.
Mills, Susan et al: "Inhibitory activity of Lactobacillus plantarum LMG P-26358 against Listeria innocua when used as an adjunct starter in the manufacture of cheese", Microbial Cell Factories, vol. 10, No. Suppl I, Aug. 1, 2011, pp. S7-S7, XP55015116.
O'Sullivan, L. et al: "Potential of bacteriocin-producing lactic acid bacteria for improvements in food safety and quality", Biochemie, Masson, Paris, FR, vol. 84, No. 5-6, May 1, 2002, pp. 593-604, XP009154979.
Papagianni, Maria: "Ribosomally synthesized peptides with antimicrobial properties: biosynthesis, structure, function, and applications" Biotechnology Advances, Elsevier Publishing, Barking, GB, vol. 21, No. 6, Sep. 1, 2003, pp. 465-499, XP004448472.
Reviriego C. et al: "A Food-Grade System for Production of Pediocin PA-1 in Nisin-Producing and Non-Nicen-Producing Lactococcus lactis Strains: Application to Inhibit Listeria Growth in a Cheese Model System", Journal of Food Protection, International Association for Food Protection, US, vol. 70, Nov. 1, 2007, pp. 2512-2517, XP009155024.
Rodriguez E et al: "Antimicrobial activity of pediocin-producing Lactococcus lactis on Listeria monocytogenes, *Staphylococcus aureus* and *Escherichia coli* 0157:117 in cheese" International Dairy Journal Elsevier Applied Science, Barking, GB, vol. 15, No. 1, Jan. 1, 2005, pp. 51-57, XP004646842.
Somkuti, G. et al: "Pediocin production in milk by Pediococcus acidilactici in co-culture with Streptococcus thermophilus and Lactobacillus delbrueckii subsp. bulgaricus", Journal of Industrial Microbiology & Biotechnology; Official Journal of the Society for Industrial Microbiology, Springer, Berlin, DE, vol. 37, No. 1, Oct. 21, 2009, pp. 65-69, XP019765109.
Van Reenen, C.A. et al: "Characterization and heterologous expression of a class IIa bacteriocin, plantaricin 423 from Lactobacillus plantarum 423, in Saccharomyces cerevisiae", International Journal of Food Microbiology, Elsevier Science Publishers, Amsterdam, NL, [Online] vol. 81, No. 1, Feb. 25, 2003, pp. 29-40, XP009122225.
Maisnier-Patin et al., "Inhibition of Listeria monocytogenes in Camembert cheese made with a nisin-producing starter," Lait, 1992, 72, 249-263.

\* cited by examiner

*Primary Examiner* — Erik Kashnikow
*Assistant Examiner* — Assaf Zilbering
(74) *Attorney, Agent, or Firm* — Foley & Lardner LLP; Sunit Talapatra

(57) ABSTRACT

The present invention discloses a method for producing a fermented dairy product, preferably cheese, comprising inoculating milk with lactic acid bacteria capable of producing a Class IIa type bacteriocin; and lactic acid bacteria capable of producing a Class I type bacteriocin.

11 Claims, No Drawings

SEQUENCE LISTING

<160> NUMBER OF SEQ ID NOS: 8

<210> SEQ ID NO 1
<211> LENGTH: 566
<212> TYPE: DNA
<213> ORGANISM: Lactobacillus plantarum
<220> FEATURE:
<221> NAME/KEY: misc_feature
<223> OTHER INFORMATION: 16S rRNA gene sequence of a strain of
      Lactobacillus plantarum deposited under number LMG P-26358
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t

<400> SEQUENCE: 1
tgagtggcga actggtgagt aacacgtggg aaacctgccc agaagcgggg       60
ggaaacagat gctaataccg cataacaact tggaccgcat ggtccgagnt tgaaagatgg      120
cttcggctat cacttttgga tggtcccgcg gcgtattagc tagatggtgg ggtaacggct      180
caccatggca atgatacgta gccgacctga gagggtaatc ggccacattg ggactgagac      240
acggcccaaa ctcctacggg aggcagcagt agggaatctt ccacaatgga cgaaagtctg      300
atggagcaac gccgcgtgag tgaagaaggg tttcggctcg taaaactctg ttgttaaaga      360
agaacatatc tgagagtaac tgttcaggta ttgacnggta tttaaccaga aagccacggc      420
taactacgtg ccagcagccg cggtaatacg taggtggcaa gcgttgtccg gatttattgg      480
gcgtaaagcg agcgcaggcg gttttttaag tctgatgtga agccttcgg ctcaaccgaa      540 aaagtgcatc ggaaactggg aaactt                                           566

<210> SEQ ID NO 2
<211> LENGTH: 19
<212> TYPE: PRT
<213> ORGANISM: Unknown
<220> FEATURE:
<223> OTHER INFORMATION: Consensus sequence comprised in N-terminal
      domain of Class IIa type bacteriocin
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

```
<220> FEATURE:
<221> NAME/KEY: misc_feature
<222> LOCATION: (15)..(18)
<223> OTHER INFORMATION: Xaa can be any naturally occurring amino acid

<400> SEQUENCE: 2

Tyr Gly Asn Gly Val Xaa Cys Xaa Xaa Xaa Xaa Cys Xaa Val Xaa Xaa
1               5                   10                  15

Xaa Xaa Ala

<210> SEQ ID NO 3
<211> LENGTH: 18
<212> TYPE: DNA
<213> ORGANISM: Unknown
<220> FEATURE:
<223> OTHER INFORMATION: 16s rRNA primer CO1

<400> SEQUENCE: 3
agtttgatcc tggctcag                                                 18

<210> SEQ ID NO 4
<211> LENGTH: 16
<212> TYPE: DNA
<213> ORGANISM: Unknown
<220> FEATURE:
<223> OTHER INFORMATION: 16s rRNA primer CO2

<400> SEQUENCE: 4
taccttgtta cgactt                                                   16

<210> SEQ ID NO 5
<211> LENGTH: 19
<212> TYPE: DNA
<213> ORGANISM: Unknown
<220> FEATURE:
<223> OTHER INFORMATION: primers 423A5

<400> SEQUENCE: 5
aaatactatg gtaatgggg                                                19

<210> SEQ ID NO 6
<211> LENGTH: 18
<212> TYPE: DNA
<213> ORGANISM: Unknown
<220> FEATURE:
<223> OTHER INFORMATION: primers 423A3

<400> SEQUENCE: 6
catggaaagt gctaatta                                                 18

<210> SEQ ID NO 7
<211> LENGTH: 21
<212> TYPE: DNA
<213> ORGANISM: Unknown
<220> FEATURE:
<223> OTHER INFORMATION: primer 423F

<400> SEQUENCE: 7
atgatgaaaa aaattgaaaa a                                             21

<210> SEQ ID NO 8
<211> LENGTH: 20
<212> TYPE: DNA
<213> ORGANISM: Unknown
```

```
<220> FEATURE:
<223> OTHER INFORMATION: primer 423R

<400> SEQUENCE: 8
cttgattatg aattaaccgt                                              20
```

ANTI-LISTERIAL MIXED CULTURE AND METHOD FOR PRODUCING CHEESE

CROSS-REFERENCE TO RELATED PATENT APPLICATIONS

European Patent Office Priority Application 11172596.6, filed Jul. 4, 2011 including the specification, claims and abstract, is incorporated herein by reference in its entirety.

BACKGROUND OF THE INVENTION

Field of the Invention

The present invention is in the field of fermenting dairy, in particular in the field of cheese production.

Driven by consumer preference, the dairy industry is constantly looking to achieve minimally processed foods which are free from artificial preservatives. In this context, much attention is being directed to preventing growth of and/or killing *Listeria* spp. with the use of bacteriocins produced by micro-organisms that are generally recognized as safe (GRAS), including many lactic acid bacteria (LAB).

Bacteriocins are ribosomally synthesized anti-microbial compounds that are produced by many different bacterial species.

One of the most well known and extensively studied bacteriocins is nisin, an FDA-approved bacteriocin produced by *Lactococcus lactis*. Maisnier-Patin et al. in Lait 1992, 72, 249-263, demonstrated the potential of using nisin-producing starters for the inhibition of *Listeria monocytogenes* in Camembert cheese. However, as acknowledged by the authors, anti-listerial effects of the nisin-producing culture could still be improved, in particular regarding prevention of regrowth of *Listeria* spp. and inhibition of *Listeria* when present at higher concentrations than $10^3$ cfu/ml. To date, nisin-producing cultures are commercially used in dairy fermentations to prevent outgrowth of *Clostridium* spp.

Whilst nisin is a representative of a Class I bacteriocin, which has broad spectrum action against gram-positive micro-organisms, Class IIa bacteriocins and their producer organisms are of considerable interest as biopreservatives due to their high anti-listerial activity. As stated in the review by L. O'Sullivan et al. in Biochimie 2002, 84, 593-604, Class IIa bacteriocins are more interesting anti-listerial agents than the Class I bacteriocins, because they do not have as broad an inhibitory spectrum and thus do not kill many starter cultures, whilst killing *Listeria* strains more effectively. However, it is also stated herein that there are limitations to the usefulness of Class IIa bacteriocins since full suppression of the pathogen is rarely achieved.

Hence, there is still room for improvement regarding inhibition and/or killing *Listeria* spp. when producing a fermented dairy product.

SUMMARY OF THE INVENTION

To this end, in a first aspect the invention provides a method for producing a fermented product, in particular a cheese, said method comprising inoculating milk with
   a. one or more strains of lactic acid bacteria capable of producing a Class IIa type bacteriocin; and
   b. one or more strains of lactic acid bacteria capable of producing a Class I type bacteriocin; and
   c. optionally, one or more further lactic acid bacterial strains.

It was found that the combination of the one or more strains of lactic acid bacteria as defined under (a.) and (b.), one capable of producing a Class IIa type and the other a Class I type bacteriocin, respectively, yielded a significantly enhanced kill-off of viable *Listeria* in fermented dairy products as compared with the anti-listerial effect achievable by inoculating the milk with said individual strains at comparable rates.

In this respect it is noted that a synergetic use of nisin and pediocin (an example of a Class IIa bacteriocin) against listerial contamination in food has been suggested by Hanlin et al. in J. Food Prot. 1993, 56, 252-255.

However, Hanlin is silent on dairy fermentations. Furthermore, Hanlin teaches the combined use of the bacteriocins per se, and is silent on the use of bacteriocin-producing micro-organisms. Since Class I-type bacteriocins are commonly known to have broad spectrum inhibition towards bacteria, including most lactic acid bacteria, including for example lactococci and lactobacilli, the production of a Class IIa bacteriocin by the Class IIa bacteriocin producing micro-organisms would be expected to be seriously impeded in the presence of a Class I bacteriocin producing strain.

The present inventors found that the combined use of bacteriocin-producing micro-organisms is much preferred over the use of the bacteriocins per se as disclosed by Hanlin, especially in dairy fermentations. Without being bound to theory, it is thought that conditions which will favour the growth of *Listeria* will generally also stimulate growth of the bacteriocin-producing strains, so that bacteriocin(s) may be present at effective levels during at least part of the shelf life of the fermented dairy product. In contrast, since fermented dairy products generally contain proteolytically positive bacteria, when Class I and/or IIa bacteriocins are added per se without being produced in situ, they can become depleted during production and/or shelf life of the fermented dairy product.

The invention also provides a mixed lactic acid bacterial culture composition comprising
   a. one or more strains of lactic acid bacteria capable of producing a Class IIa type bacteriocin; and
   b. one or more strains of lactic acid bacteria capable of producing a Class I type bacteriocin; and
   c. optionally, one or more further lactic acid bacterial strains.

In one embodiment the one or more strains of lactic acid bacteria capable of producing a Class IIa type bacteriocin is/are different from the one or more strains of lactic acid bacteria capable of producing a Class I type bacteriocin. Advantageously this allows the selection of different suitable wild type strains. Furthermore, selecting at least two different strains producing different bacteriocins improves the intrisic protection against spoilage by *Lysteria* spp. in case a strain would be eliminated by for example a phage contamination giving. In a mixed lactic acid bacterial culture the chances are better that at least one bacteriocin producing strain remains as protection against *Lysteria* spp.

The invention furthermore provides a cheese obtainable by the method according to the invention.

The invention also provides a strain of *Lactobacillus plantarum* deposited under number LMG P-26358 or a mutant thereof which has the capability to produce a Class IIa type bacteriocin and preferably has at least 95%, more preferably at least 97%, more preferably 100% 16S rRNA similarity, preferably identity, with said deposited strain. In the method of the invention, this strain works extremely well with a Type 1 producing lactic acid bacterial strain in producing a bacteriocin mixture which is highly effective against *Listeria*. Furthermore a cheese of very good taste can be obtained.

The invention further provides a bacterial culture composition comprising viable bacteria of *Lb. plantarum* deposited under number LMG P-26358, or mutants thereof capable of producing a Class IIa type bacteriocin, preferably at a viable cell count of $1.10^8$ cfu/ml or higher, such as $1.10^9$ cfu/ml or higher. In the method of the invention, the strain of *Lb. plantarum* deposited under number LMG P-26358 is preferably provided in the form of such a bacterial culture composition.

DETAILED DESCRIPTION OF THE INVENTION

Definitions

In the context of this invention, the term "viable cell count" is held to mean "colony forming unit (cfu) density" expressed as cfu per volume or cfu per weight. The term "lactic acid bacteria" is known to the person skilled in the art. In the context of this invention, the term "lactic acid bacteria" is preferably defined as Gram-positive, non-spore-forming, anaerobic or facultatively anaerobic, catalase negative cocci or rods capable of forming lactic acid as an end product of their carbohydrate metabolism. Well-known genera include *Bifidobacterium*, *Carnobacterium*, *Enterococcus*, *Lactobacillus*, *Lactococcus*, *Lactospaera*, *Leuconostoc*, *Oenococcus*, *Pediococcus*, *Streptococcus*, *Vagococcus* and *Weissella*. All lactic acid bacteria described herein are capable of fermenting lactose, and thus to convert lactose into amongst others glucose as one of the first steps in their lactose metabolism. Lactic acid bacteria may be classified as homofermentative or heterofermentative. These definitions are known to the skilled person. The expressions "heterofermentative" and "homofermentative" when related to lactic acid bacteria are preferably defined as in the handbook "Bacterial Starter Cultures for Foods," Stanley E. Gilliland, CRC Press, Boca Raton, Second Printing, 1986, Chapter 2, especially pp. 8-11. Pages 8-11, the references to Orla-Jensen and to Kandler, and especially FIG. 3 on p. 11 are especially relevant and are incorporated by reference herein. Preferably, when grown in 10% reconstituted skim milk, homofermentative lactic acid bacteria will produce lactic acid almost exclusively via the hexose diphosphate pathway. Preferably, when grown in 10% reconstituted skim milk, heterofermentative lactic acid bacteria will additionally and/or alternatively to the hexose diphosphate pathway use a pathway wherein glucose is decarboxylated and a pentose sugar is formed; the pentose will then be cleaved into a C3 and a C2 fragment, the C3 fragment finally being reducable to lactic acid; the C2 fragment may end up as acetate or may be further reduced e.g. in the production of acetaldehyde and/or ethanol. Preferably, in homofermentative lactic acid bacteria, during growth in 10% reconstituted milk, more than 95%, more preferably more than 98%, yet more preferably more than 99% of lactic acid is produced via the hexose diphosphate pathway, and thus via pyruvate as an intermediate. Preferably, during growth in 10% reconstituted milk, in heterofermentative lactic acid bacteria, more than 5%, more preferably more than 10%, yet more preferably more than 15% or even more than 50% or more than 80% of lactic acid is produced via a metabolic pathway involving a pentose-containing intermediate.

Representative heterofermentative lactic acid bacterial species include *Leuconostoc* spp., *Oenococcus* spp., *Weissella* spp., and *Lactobacillus* spp. selected from the group consisting of *Lactobacillus casei*, *Lactobacillus curvatus*, *Lb. plantarum*, *Lactobacillus paraplantarum*, *Lactobacillus pentosus*, *Lactobacillus sakei*, *Lactobacillus brevis*, *Lactobacillus buchneri*, *Lactobacillus fermentum*, and *Lactobacillus reuteri*. Representative homofermentative lactic acid bacterial species include *Lactococcus* spp., *Enterococcus* spp., *Streptococcus* spp., *Pediococcus* spp., and *Lactobacillus* spp. selected from the group consisting of *Lactobacillus acidophilus*, *Lactobacillus delbrueckii*, *Lactobacillus helveticus*, and *Lactobacillus salivarius*.

Lactic acid bacteria may additionally form other metabolites such as bacteriocins, exopolysaccharides and/or flavour compounds.

The expression "Class IIa type bacteriocin" is known to the skilled person and preferably relates to a ribosomally synthesized antilisterial peptide carrying a disulfide bond or bridge. An example of a Class IIa type bacteriocin is pediocin. Other Class IIa type bacteriocins are known as pediocin-like bacteriocins. Class IIa type bacteriocins are distinguished from Class IIb type bacteriocins in that the latter require two peptides for antilisterial activity. Class IIc type bacteriocins are circular.

A Class I type bacteriocin is known to the person skilled in the art, and preferably relates to a lantibiotic or to a lanthionine or methyllanthionine containing peptide bacteriocin. The lanthionine or methyllanthionine containing peptide bacteriocin preferably has a molecular weight <10 kDa. Nisin is one of the most important Class I type bacteriocins. The activity of nisin is conveniently expressed in units or as IU, in which 40 units or 40 IU corresponds with 1 μg of pure nisin. The expression "nisin" may be read as "a nisin" and may relate to any nisin, for example relate to nisin A or nisin Z. Preferably, "nisin" relates to nisin A. Preferably "a nisin" relates to nisin A.

Herein, the expression "milk" refers to any milk. The milk preferably comprises or more preferably consists of raw milk. Raw milk is very susceptible to listerial contamination. Said—preferably raw—milk is preferably selected from cow milk, sheep milk, or goat milk, or is provided as a mixture containing two or more of said types of milk.

Sequence similarity or identity is preferably determined using BLAST. BLAST is a well known algorithm and is described in Altschul, S. F., Gish, W., Miller, W., Myers, E. W. & Lipman, D. J. (1990) "Basic local alignment search tool." J. Mol. Biol. 215:403-410.

Similarity or identity between DNA or RNA sequences is preferably determined according to a nucleotide-nucleotide BLAST algorithm known as BLASTn using default parameters and available via the BLAST website of the NCBI, at the time of writing this algorithm is accessible via http://blast.ncbi.nlm.nih.gov/Blast.cgi?CMD=Web&PAGE_TYPE=BlastHome (incorporated by reference).

Similarity or identity between amino acid sequences is preferably determined according to a protein-protein BLAST algorithm known as BLASTp using default parameters and available via the BLAST website of the NCBI, at the time of writing this algorithm is accessible via http://blast.ncbi.nlm.nih.gov/Blast.cgi?CMD=Web&PAGE_TYPE=BlastHome (incorporated by reference).

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one."

Strains of Lactic Acid Bacteria Capable of Producing a Class IIa Type Bacteriocin
Heterofermentative Strains May be Favourably Used.

Advantageously, at least one of the strains of lactic acid bacteria capable of producing a Class IIa type bacteriocin is heterofermentative. It is especially preferred that at least one of the strains of lactic acid bacteria capable of producing a Class IIa type bacteriocin is selected from the group consisting of *Leuconostoc* spp., *Oenococcus* spp., *Weissella* spp., and *Lactobacillus* spp. wherein said *Lactobacillus* spp. is selected from the group consisting of *Lb. casei, Lb. curvatus, Lb. plantarum, Lb. paraplantarum, Lb. pentosus, Lb. sakei, Lb. brevis, Lb. buchneri, Lb. fermentum*, and *Lb. reuteri*.

Preferably, the total population of lactic acid bacteria capable of producing a Class IIa type bacteriocin comprises 10-100% of heterofermentative lactic acid bacteria (the remainder being homofermentative lactic acid bacteria); the percentage is preferably expressed as 100 times the viable cell count of the heterofermentative lactic acid bacterial population divided by the viable cell count of the total lactic acid bacterial population. Herein, said heterofermentative bacteria are preferably selected from the group consisting of *Leuconostoc* spp., *Oenococcus* spp., *Weissella* spp., and *Lactobacillus* spp. wherein said *Lactobacillus* spp. are selected from the group consisting of *Lb. casei, Lb. curvatus, Lb. plantarum, Lb. paraplantarum, Lb. pentosus, Lb. sakei, Lb. brevis, Lb. buchneri, Lb. fermentum*, and *Lb. reuteri*.

Heterofermentative lactic acid bacteria per se are not generally desired in cheese making since heterofermentative metabolism of lactose generally produces $CO_2$ and/or sometimes unwanted by products such as acetic acid, acetic aldehyde and/or ethanol. The production of these metabolites is not generally desirable for cheese, especially if a cheese with not too many and/or too large holes or eyes is desired, and/or if a cheese with a clean flavour is desired. However, in the presence of the one or more strains of lactic acid bacteria capable of producing a Class I type bacteriocin, unwanted $CO_2$ production and/or the formation of off-flavours—which could or would be caused by the heterofermentative bacteria in the absence of the Class I type bacteriocin—can be reduced or prevented.

Lactobacilli are Especially Preferred.

In another preferred embodiment, at least one of the strains of lactic acid bacteria capable of producing a Class IIa type bacteriocin is selected from the group consisting of *Lactobacillus* spp., and is especially preferably selected from the group consisting of *Lb. curvatus, Lb. plantarum, Lb. paraplantarum, Lb. pentosus, Lb. sakei, Lb. brevis, Lb. buchneri, Lb. fermentum, Lb. reuteri*, and *Lb. paracasei*. Preferably, *Lactobacillus* spp. and especially the *Lactobacillus* spp. selected from the group consisting of *Lb. curvatus, Lb. plantarum, Lb. paraplantarum, Lb. pentosus, Lb. sakei, Lb. brevis, Lb. buchneri, Lb. fermentum, Lb. reuteri*, and *Lb. paracasei* are present at a viable cell count of 30-100% of the total viable cell count of all lactic acid bacteria capable of producing a Class IIa type bacteriocin. Preferably said *Lactobacillus* spp. is present at a viable cell count of 50-100%, more preferably 70-100%, more preferably 90-100%, more preferably about 100%, of the total viable cell count of all lactic acid bacteria capable of producing a Class IIa type bacteriocin.

Lactobacilli, especially lactobacilli selected from the group consisting of *Lb. curvatus, Lb. plantarum, Lb. paraplantarum, Lb. pentosus, Lb. sakei, Lb. brevis, Lb. buchneri, Lb. fermentum, Lb. reuteri*, and *Lb. paracasei*, may be capable to produce sulphury-type notes or other kinds of off-flavours which in many cases are unwanted. Surprisingly, it has been found that the occurrence of said off-flavours is reduced or even prevented in the presence of a Class I type bacteriocin-producing strain, thereby producing a cheese having better control of eye formation and/or with reduced off-taste as compared with a cheese not comprising the Class I type bacteriocin-producing strain.

Strains Capable of Producing a Class IIa Type Bacteriocin are Preferably Sensitive to the Class I Type Bacteriocin.

Enhanced listerial kill can be obtained if at least one, or even all of the strains of lactic acid bacteria capable of producing a Class IIa type bacteriocin are sensitive to the Class I bacteriocin(s) produced by the one or more strains capable of producing a Class I type bacteriocin. Herein, the Class I bacteriocin preferably comprises, or is, a nisin.

In the context of this invention, a strain of lactic acid bacteria capable of producing a Class IIa type bacteriocin and that is sensitive to the Class I bacteriocin(s) produced by the one or more strains capable of producing a Class I type bacteriocin, is a strain which, when cultured at its optimal growth temperature during 4 h in 10% reconstituted skimmed milk, grows in the absence of nisin to a colony forming unit density which is at least 5 times higher than the colony forming unit density that is reached when the same strain is incubated in the presence of 320 IU/ml of nisin under otherwise the same conditions. If necessary for optimal growth, the reconstituted skim milk is supplemented with 0.1% yeast extract and/or 0.2 $g \cdot l^{-1}$ $MnSO_4.4H_2O$.

In a preferred embodiment according to the invention, the strain of lactic acid bacteria capable of producing a Class IIa type bacteriocin grows, when cultured at its optimal growth during 4 h temperature in 10% reconstituted skimmed milk in the absence of nisin to a colony forming unit density which is at least 5 times higher than the cell count that is reached when the same strain is incubated in the presence of 320 IU/ml of nisin under otherwise the same conditions. Optionally the reconstituted skimmed milk is supplemented with 0.1% yeast extract and/or 0.2 $g \cdot l^{-1}$ $MnSO_4.4H_2O$ in case this is needed for optimal growth.

It has been surprisingly found that even if a lactic acid bacterial strain capable of producing a Class IIa type is sensitive, to a Class I type bacteriocin, it will be inhibited by the Class I bacteriocin-producing strain but the production of the Class IIa bacteriocin and thereby effective kill-of listerial species is still achieved. Said capacity for production of a Class IIa type bacteriocin in the presence of a strain capable of producing a Class I type bacteriocin is especially achieved in the method according to the invention if the milk is directly inoculated with:

at least one, and preferably all of the strains of lactic acid bacteria capable of producing a Class I type bacteriocin are provided in frozen or freeze-dried form, and at least one, and preferably all of the strains of lactic acid bacteria capable of producing a Class IIa type bacteriocin are provided in frozen or freeze-dried form.

Herein the expression "directly inoculated" is known to the skilled person and has the same meaning as in "direct vat inoculation" and means that the frozen or freeze-dried bacteria, prior to their addition to the milk, are not allowed to achieve growth by more than 1 (one) log unit, more preferably by more than 0.2 log units. The frozen or freeze-dried bacteria may nevertheless be optionally thawed, or dissolved in an aqueous medium, prior to being added to the milk.

It has been found that lactobacilli—even if sensitive to nisin or another Class I type bacteriocin—are especially capable to survive well in cheese obtained using the method, keeping viable *Lactobacillus* cell counts of $1.10^6$ cfu/g or higher or even of $1.10^7$ cfu/g or higher during up to 18 weeks after its production, especially when the cheese is kept at a temperature of between 2 and 18° C., yet more preferably between 4 and 15° C.

Particularly Preferred Strains Capable of Producing a Class IIa Type Bacteriocin.

It is particularly preferred that at least one of the lactic acid bacteria capable of producing a Class IIa type bacteriocin is a strain of *Lactobacillus plantarum*, or is a lactic acid bacterial strain, having a 16S rRNA gene with a sequence that has more than 95%, preferably more than 97%, more preferably more than 99% similarity, preferably identity, or most preferably having 100% similarity, preferably identity, with the SEQ ID NO 1. SEQ ID NO 1 is the 16S rRNA gene sequence of the *Lactobacillus plantarum* deposited under number LMG P-26358.

It is especially preferred that at least one of the lactic acid bacteria capable of producing a Class IIa type bacteriocin is the strain *Lactobacillus plantarum* deposited under number LMG P-26358 or a mutant thereof which has the capability to produce a Class IIa type bacteriocin and preferably has 100% 16S rRNA gene similarity, preferably identity, with SEQ ID NO 1.

In an especially further preferred embodiment, strains of *Lactobacillus plantarum* or lactic acid bacterial strains having a 16S rRNA gene with a sequence that has more than 95%, preferably more than 97%, more preferably more than 99% similarity, preferably identity, or most preferably having 100% similarity, preferably identity, with SEQ ID NO 1, are present at a viable cell count which is 30-100%, preferably 50-100%, more preferably 70-100%, more preferably 90-100%, more preferably about 100%, of the total viable cell count of all lactic acid bacteria capable of producing a Class IIa type bacteriocin. It is particularly preferred that the strain is *Lactobacillus plantarum* deposited under number LMG P-26358 or a mutant thereof which has the capability to produce a Class IIa type bacteriocin and preferably has 100% 16S rRNA gene similarity, preferably identity, with SEQ ID NO 1.

In these preferred embodiments, optimal taste, texture and antilisterial effect can be obtained in a method of producing cheese, especially if the Class I type bacteriocin(s) produced by the one or more lactic acid bacterial strains in (b) comprises or consists of a nisin.

Strains of Lactic Acid Bacteria Capable of Producing a Class I Type Bacteriocin

Preferably at least one of the strains of lactic acid bacteria capable of producing a Class I type bacteriocin is selected from the group consisting of *Lactococcus* spp., or preferably is selected as a strain of *Lactococcus* lactis subsp. *lactis* biovar *diacetylactis*. Thus in one embodiment the invention concerns a method for producing a fermented dairy product, preferably cheese, said method comprising inoculating milk with a one or more strains of lactic acid bacteria capable of producing a Class IIa type bacteriocin; and
    b one or more strains of lactic acid bacteria capable of producing a Class I type bacteriocin; and
    c optionally, one or more further lactic acid bacterial strains, wherein at least one of the strains of lactic acid bacteria capable of producing a Class IIa type bacteriocin is selected from the group consisting of *Lactobacillus* spp., and wherein at least one of the strains of lactic acid bacteria capable of producing a Class I type bacteriocin is selected from the group consisting of *Lactococcus* spp.

In one embodiment, the Class I type bacteriocin producing strain is not capable of producing a bacteriocin that is different from a Class I type bacteriocin. In one embodiment, the Class I type bacteriocin producing strain is capable of a single bacteriocin.

Further preferably at least one of the strains of lactic acid bacteria capable of producing a Class I type bacteriocin is a lactic acid bacterial strain which is capable to produce a nisin or a lacticin, most preferably a nisin. In one embodiment, the Class I type bacteriocin producing strain is capable of only producing nisin as a single bacteriocin.

It is especially preferred that at least one of the strains of lactic acid bacteria capable of producing a Class I type bacteriocin is a strain of *L. lactis*, such as a strain of *L. lactis* subsp. *lactis* biovar *diacetylactis*, that is capable of producing a nisin and that is immune to nisins, whereby further preferably the capability to produce nisin and the nisin-immunity are encoded by genetic information that is present on, or derived from a transposon, such as preferably Tn5276-NI.

The term "nisin-producing strain" or equivalently "strain capable of producing a nisin" preferably relates to a lactic acid bacterial strain which is capable, optionally in the presence of a yeast extract, to produce at least 10 IU, more preferably at least 100 IU, most preferably at least 300 IU of a nisin per ml of (pasteurised) milk during incubation of said milk for 24 hours at 30° C., wherein the milk has been inoculated with the nisin-producing strain at about $10^6$ cfu/ml. Preferably within the context of this invention the term "nisin-producing strain" or equivalently "strain capable of producing a nisin" relates to a lactic acid bacterial strain which is capable, optionally in the presence of a yeast extract, to produce at least 100 IU, more preferably at least 300 IU of a nisin per ml of pasteurised milk during incubation of said milk for 8 hours at 30° C., wherein the milk has been inoculated with the nisin-producing strain at about $10^6$ cfu/ml.

In an especially further preferred embodiment, nisin-producing strains of *L. lactis* and/or further (sub)species thereof are present at a viable cell count which is 30-100%, preferably 50-100%, more preferably 70-100%, more preferably 90-100%, more preferably about 100%, of the total viable cell count of all lactic acid bacteria capable of producing a Class I type bacteriocin.

A concentrated culture comprising bacteria of a nisin-producing, nisin-immune strain of *L. lactis* subsp. *lactis* biovar *diacetylactis* and of a nisin-immune strain of *L. lactis* subsp. *cremoris* each at a viable cell count of at least $1.10^9$ cfu/ml is commercially available, for example as D509, from the DairySafe range of CSK Food Enrichment BV, The Netherlands.

Nisin-producing lactococcal cultures may for instance also be obtained from Chr. Hansen, for example as BS-10. Nisin-producing lactococcal cultures are also known in the literature for example from Bouksaim et al., 2000, Int. J. Food Microbiol. vol. 59, pp. 141-156).

The Optionally One or More Further Lactic Acid Bacterial Strains

In the method of producing a fermented dairy product, preferably a cheese, according to the present invention, either of the bacteriocin producing strains as defined under (a) and (b) also are capable of acidifying and thus are suitable to be included as a single-strain acidifying starter culture in the production of cheese.

In an embodiment of the method according to the invention and/or in an embodiment of the mixed lactic acid bacterial culture composition according to the invention, besides the Class IIa type bacteriocin and Class I type bacteriocin producing strains, one or more further lactic acid bacterial strains are present. Preferably the one or more further lactic acid bacterial strains are lactococcal acidifying strains. Preferably the one or more further lactic acid bacterial strains are resistant or immune to Class I type bacteriocins, preferably the one or more further lactic acid bacterial strains are resistant or immune to nisin.

A lactococcal acidifying strain that is resistant or immune to a Class I type bacteriocin, in particular resistant or immune to nisin, relates to a lactococcal strain which, when added to pasteurised milk in an amount of 1 wt. % with respect to the weight of the milk, in the presence of a Class I type bacteriocin, in particular nisin, at 10 units/ml, is capable of reducing the pH of the milk by at least 1 pH unit during incubation of the milk for 6 hours at a temperature of 30° C.

In an embodiment, a further lactic acid bacterial strain that is present, is a nisin-immune strain of *L. lactis*, preferably of subspecies *cremoris*. The immunity to nisin in this strain is preferably encoded by genetic information that is present on, or derived from a transposon, such as e.g. Tn5276-NI. A concentrated culture comprising bacteria of a nisin-producing strain of *L. lactis* subsp. *lactis* biovar *diacetylactis* and of a nisin-immune strain of *L. lactis* subsp. *cremoris* each at a viable cell count of about $1.10^{10}$ cfu/ml is commercially available, for example as D509, from the DairySafe range of CSK Food Enrichment BV, The Netherlands.

Additionally or alternatively, in an embodiment one or more further lactic acid bacterial strains that are present are one or more strains of *Lb. helveticus* and/or of *Lb. acidophilus*. Accordingly, an even better taste of a cheese can be obtained in a method for making the cheese. A concentrated culture comprising bacteria of *Lb. helveticus* at a viable cell count of at least $1.10^9$ cfu/ml is commercially available, for example as L700, from CSK Food Enrichment BV, The Netherlands.

Specific Preferred Embodiments for the Mixed Culture.

The mixed lactic acid culture composition according to the invention preferably consists of (1) lactic acid bacteria; (2) water; (3) optionally non-lactic acid bacteria, preferably at a total viable cell count of less than $10^4$ cfu/g of the composition, and (4) optionally further additives in an amount of up to 20 wt. % relative to the weight of the composition.

In one embodiment the mixed lactic acid bacterial culture composition comprises
   a one or more strains of lactic acid bacteria capable of producing a Class IIa type bacteriocin; and
   b one or more strains of lactic acid bacteria capable of producing a Class I type bacteriocin; and
   c optionally, one or more further lactic acid bacterial strains,
wherein at least one of the strains of lactic acid bacteria capable of producing a Class IIa type bacteriocin is selected from the group consisting of *Lactobacillus* spp., and wherein at least one of the strains of lactic acid bacteria capable of producing a Class I type bacteriocin is selected from the group consisting of *Lactococcus* spp.

The lactic acid bacteria are preferably present at a viable cell count of at least $1.10^9$ cfu/g, more preferably of at least $1.10^{10}$ cfu/g of the composition. The optional further additives preferably comprise a cryoprotectant, such as a monosaccharide, and/or a disaccharide, and/or an oligosaccharide such as inulin and/or a polysaccharide such as gum arabic or xanthan gum, or a mixture thereof. The cryoprotectant is preferably present in an amount of 1-15 wt. % relative to the weight of the composition.

The mixed lactic acid culture composition is preferably in frozen or freeze-dried form. However, the mixed lactic acid bacterial culture composition may also be in liquid form. When in frozen form, the mixed lactic acid culture composition is preferably in the form of frozen particles further preferably having a diameter of from about 0.01 mm to about 50 mm, yet more preferably of from about 0.1 mm to about 10 mm. Such particles are commonly known as pellets.

Preferably, at least one of the lactic acid bacterial strains is capable to produce a nisin and at least one of the strains of the lactic acid bacteria capable of producing a Class IIa type bacteriocin is not capable of growing in the presence of the nisin at a concentration of 300 IU·ml$^{-1}$, more preferably at a concentration of the nisin of 500 IU·mL$^{-1}$.

Further preferably at least one of the strains of lactic acid bacteria capable of producing a Class IIa type bacteriocin is present as a strain of *Lb. plantarum* deposited under number LMG P-26358 or a mutant thereof which has the capability to produce a Class IIa type bacteriocin and preferably has 100% 16S rRNA gene similarity, preferably identity, with said deposited strain; and at least one of the strains of lactic acid bacteria capable of producing a Class I type bacteriocin is selected from the group consisting of *Lactococcus* spp., preferably as a strain of *L. lactis* subsp. *lactis* biovar *diacetylactis*, and is a strain which is capable of producing a nisin.

The one or more strains of lactic acid bacteria capable of producing a Class IIa type bacteriocin are preferably present in the culture composition at a total viable cell count of at least $1.10^7$, more preferably of at least $1.10^8$, most preferably of at least $1.10^9$ cfu per gram of the culture composition, and the one or more strains of lactic acid bacteria capable of producing a Class I type bacteriocin are preferably present in the culture composition at a total viable cell count of at least $1.10^7$, more preferably of at least $1.10^8$, most preferably of at least $1.10^9$ cfu per gram of the culture composition. Especially good results in terms of taste and bacteriocin production can be obtained if the ratio of viable lactic acid bacteria capable of producing a Class IIa type bacteriocin to viable lactic acid bacteria capable of producing a Class I type bacteriocin is between 50:1-1:2, more preferably of between 30:1-1:1, most preferably 20:1-3:1. These ratios are also preferably used in the method for producing the fermented dairy product.

The mixed lactic acid bacterial culture composition preferably comprises under (a) the strain of *Lb. plantarum* deposited under number LMG P-26358 or a mutant thereof which has the capability to produce a Class IIa type bacteriocin and preferably has 100% 16S rRNA gene similarity, preferably identity, with said deposited strain at a total viable cell count of preferably at least $1.10^8$, more preferably of at least $1.10^9$ cfu per gram of the culture composition, and preferably additionally comprises under (b) a strain of *Lactococcus* spp., preferably a strain of *L. lactis* subsp. *lactis* biovar *diacetylactis*, said lactococcal strain being capable of producing a nisin, and said lactococcal strain being present at a total viable cell count of at least $1.10^8$, more preferably of at least $1.10^9$ cfu per gram of the culture composition.

Under (c), the mixed lactic acid bacterial culture composition preferably further comprises one or more strains of *Lb. helveticus* and/or of *Lb. acidophilus*. The viable cell count of said one or more strains of *Lb. helveticus* and/or of *Lb. acidophilus* in the culture composition is preferably at least $1.10^8$, more preferably at least $1.10^9$ cfu per gram of the culture composition. Additionally or alternatively to the one or more strains of *Lb. helveticus* and/or of *Lb. acidophilus*, the mixed lactic acid bacterial culture composition preferably comprises a nisin immune or nisin resistant lactococcal acidifying strain, preferably at a viable cell count of at least $1.10^9$ cfu per gram of the culture composition. A concentrated culture comprising bacteria of *Lb. helveticus* at a viable cell count of at least $1.10^9$ cfu/ml is commercially available, for example as L700, from CSK Food Enrichment BV, The Netherlands.

Best results, especially in terms of anti-listerial effect and taste of a cheese produced therewith, are obtained if the mixed lactic acid bacterial culture composition comprises a nisin-producing lactococcal strain, optionally a nisin-immune or resistant lactococcal strain, and the strain of *Lb. plantarum* LMG P-26358, wherein bacteria of each of said strains are present at least $1.10^8$ cfu/ml, more preferably at least $1.10^9$ cfu/ml of the culture composition, and wherein the ratio of viable bacteria of *Lb. plantarum* LMG P-26358 to viable nisin-producing lactococci is between 50:1-1:2, more preferably between 30:1-1:1, most preferably between 20:1-3:1. These ratios are also preferably used in the method for producing the fermented dairy product.

The Class IIa Type Bacteriocin

The Class IIa type bacteriocin preferably comprises a N-terminal domain comprising the consensus sequence SEQ ID NO 2: YGNGV(X)C(X)$_4$C(X)V(X)$_4$A wherein X represents any amino acid. Herein, each letter codes for an amino acid according to the single-letter coding scheme for amino acids known to the skilled person.

The Class IIa type bacteriocin preferably has a molecular weight of 3929+/−4 Dalton. The Class IIa type bacteriocin is preferably selected from the group consisting of a plantaricin, a pediocin, a sakacin, a mesentericin, a carnobacteriocin, a curvacin, a leucocin and an enterocin. Preferably, the Class IIa type bacteriocin has an amino acid sequence which has 95% similarity, preferably identity, or higher, more preferably 97% similarity, preferably identity, or higher, most preferably 99% similarity, preferably identity, or even about 100% similarity, preferably identity with the amino acid sequence of having a molecular mass of 3932.74 as described by Van Reenen et al. in Int. J. Food Microbiol. 2003, vol. 81, pp. 29-40. The amino acid sequence of the bacteriocin produced by the strain of *Lb. plantarum* deposited under number LMG P-26358 has at least 99% similarity, preferably identity, with the amino acid sequence of plantaricin 423.

The Fermented Product

The invention also concerns a fermented dairy product, preferably a cheese, obtainable by the method according to the present invention wherein said fermented product comprises viable lactic acid bacteria capable of producing a Class IIa type bacteriocin and viable lactic acid bacteria capable of producing a Class I type bacteriocin. In one embodiment the at least one of the strains of lactic acid bacteria capable of producing a Class IIa type bacteriocin is selected from the group consisting of *Lactobacillus* spp., and at least one of the strains of lactic acid bacteria capable of producing a Class I type bacteriocin is selected from the group consisting of *Lactococcus* spp.

The fermented product preferably comprises viable lactic acid bacteria capable of producing a Class IIa type bacteriocin in an amount of at least $1.10^6$ cfu/g, more preferably of at least $1.10^7$ cfu/g, most preferably of at least $1.10^8$ cfu/g of fermented dairy product. Accordingly best anti-listerial results can be obtained. It has been observed that at viable cell counts of below $1.10^8$ and especially of below $1.10^7$ or below $1.10^6$ cfu/g of fermented dairy product, the antilisterial effect is noticeably reduced, especially if the viable lactic acid bacteria capable of producing a Class IIa type bacteriocin are selected as *Lactobacillus* spp. Preferably the fermented product further comprises viable lactic acid bacteria capable of producing a Class I type bacteriocin in an amount of at least $1.10^6$ cfu per gram of fermented dairy product. The fermented product is preferably a cheese, most preferably a semi-hard cheese or a hard cheese. The semi-hard cheese or hard cheese is preferably selected from the group consisting of Gouda-type cheese, Cheddar-type cheese, Tilsit, and Gruyere. The expression Gouda-type cheese comprises all semi-hard and hard cheeses obtained by a cheese-making process comprising salting in brine solution, such as Gouda, Edam, and Maasdam.

The Deposited Strain and the Bacterial Culture Comprising the Deposited Strain

The strain *Lb. plantarum* LMG P-26358 has been isolated from the surface of a soft French artisanal cheese. A slice of this cheese was cut consisting of surface and about 1 cm of cheese beneath and the strain was isolated from this slice. Said strain is a lactic acid bacterium and was deposited on 17 Mar. 2011 under the terms of the Budapest Treaty on the International Recognition of the Deposit of Microorganisms for the Purposes of Patent Procedures at Belgian Coordinated Collections of Micro-organisms (BCCM™), Laboratorium voor Microbiologie—Bacteriënverzameling, Universiteit Gent, K. L. Ledeganckstraat 35, B-9000 Gent, Belgium. It was assigned deposit number LMG P-26358. The anti-listerial bacteriocin produced by LMG P-26358 was determined in an agar well diffusion assay using *Enterococcus faecalis* DPC 5055/LMG 7973 or more preferably *Listeria innocua* as the indicator organism.

The scope of the present invention also encompasses a mutant of the deposited strain of *Lb. plantarum* LMG P-26358 which mutant preferably has the capability to produce a Class IIa type bacteriocin, preferably the same Class IIa type bacteriocin as said deposited strain, and/or preferably has at least 95%, preferably at least 97%, more preferably 100% 16S rRNA gene similarity with said deposited strain. Herein the expression "mutant" is known to the skilled person and preferably relates to a strain of *Lb. plantarum* obtained by mutation, variation or recombination of the deposited strain of *Lb. plantarum* LMG P-26358.

The present invention also provides a bacterial culture composition comprising viable bacteria of *Lb. plantarum* LMG P-26358 or a mutant thereof, said mutant preferably having at least 95%, preferably at least 97%, more preferably about 100% 16S rRNA gene similarity with said strain. Additionally, it is preferred that said mutant has the capability to produce the same Class IIa type bacteriocin as the strain of *Lb. plantarum* LMG P-26358. The bacterial culture composition preferably comprises the viable bacteria of *Lb. plantarum* LMG P-26358 or the mutant thereof at a viable count of at least $1.10^8$ cfu/ml, more preferably of at least $1.10^9$ cfu/ml, most preferably of at least $1.10^{10}$ cfu/ml of the culture composition; the viable count of the *Lb. plantarum* LMG P-26358 or the mutant thereof will in practical conditions reside below $1.10^{12}$ cfu/ml of the culture composition.

This bacterial culture composition is preferably in frozen or freeze-dried form. A frozen or freeze-dried culture is easy to store until use. When in frozen form, the mixed lactic acid culture composition is preferably in the form of frozen particles further preferably having a diameter of from about 0.01 mm to about 50 mm, yet more preferably of from about 0.1 mm to about 10 mm. Such particles are commonly known as pellets.

Alternatively, this bacterial culture composition may also be in liquid form. The liquid form is particularly advantageous in a method comprising applying this liquid bacterial culture composition to the surface of a cheese. The invention also discloses a cheese obtainable by this method.

This bacterial culture composition preferably consists of (1) lactic acid bacteria comprising *Lb. plantarum* LMG P-26358; (2) water; (3) optionally non-lactic acid bacteria, preferably at a total viable cell count of less than $10^4$ cfu/g of the composition, and (4) optionally further additives in an amount of up to 20 wt. % relative to the weight of the composition. The lactic acid bacteria are preferably present at a viable cell count of at least $1.10^9$ cfu/g, more preferably of at least $1.10^{10}$ cfu/g of the culture composition. The optional further additives preferably comprise a cryoprotectant, such as a monosaccharide, and/or a disaccharide, and/or an oligosaccharide such as inulin and/or a polysaccharide such as gum arabic or xanthan gum, or a mixture thereof. The cryoprotectant is preferably present in an amount of 1-15 wt. % relative to the weight of the culture composition.

For all deposited microbial organisms mentioned in the present patent application the following applies. As regards the respective Patent Offices of the respective designated states, the applicants request that a sample of the deposited microorganisms stated above only be made available to an expert nominated by the requester until the date on which the patent is granted or the date on which the application has been refused or withdrawn or is deemed to be withdrawn.

In particular it is requested that a sample of the deposited microorganism will be made available until the publication of the mention of the grant of the European patent or until the date on which application has been refused or withdrawn or is deemed to be withdrawn, only by the issue of such a sample to an expert nominated by the person requesting the sample, and approved either i) by the Applicant and/or ii) by the European Patent Office, whichever applies (Rule 32 EPC).

Further Aspects of the Invention

The invention also provides a semi-hard cheese comprising the deposited strain of *Lb. plantarum* LMG P-26358, preferably at a cell count of at least $1.10^7$ cfu/g of cheese. It has been found that on a semi-hard cheese comprising said strain, the tendency for fungal outgrowth on the surface of said cheese is significantly reduced. The semi-hard cheese is preferably selected from the group consisting of a Cheddar-type cheese and a Gouda-type cheese, including Maasdam and Edam cheese.

EXAMPLES

Materials and Methods

Isolation of *Lactobacillus plantarum* LMG P-26358 and Bacteriocin Assays

Approximately 1 g of a soft artisanal French cheese was homogenized in 9 ml of maximum recovery diluent (MRD), serially diluted and plated on MRS (de Man, Rogosa, Sharpe) agar (Difco Laboratories, Detroit, Mich., USA) and grown at 30° C. for 2-3 days. Colonies that developed were overlaid with ~10 ml of GM17 agar [M17 medium (Difco Laboratories) supplemented with 0.5% (w/v) glucose] inoculated at 0.25% with an overnight culture of *L. innocua* (DPC6579). The plates were incubated for another 18 h at 37° C. and inspected for zones of inhibition of the overlaid culture. Colonies showing a clear zone of inhibition were sub-cultured into fresh MRS broth having first been removed from the agar overlay using a sterile scalpel blade. Pure cultures were obtained by streaking onto MRS agar. Bacteriocin assays and estimation of bacteriocin activity in activity units (au)/ml were performed by the agar well diffusion assay (WDA) as described by Ryan et al. et al. in Appl. Environ. Microbiol. 1996, 62, pp. 612-619. The source of each indicator organism tested for inhibition spectra is listed in Table 1 with the appropriate growing conditions. The sensitivity of a strain to bacteriocin produced by the artisanal French cheese isolates was scored according to the diameter of the zone of inhibition surrounding that producer. Each assay was performed in triplicate. Other media used in the study included BHI (Brain-Heart Infusion) broth (Oxoid Ltd., Basingstoke, Hampshire, England), RCM (Re-inforced Clostridial Medium) (Merck, Darmstadt, Germany), LBS (*Lactobacillus* Selective) agar (Difco Laboratories), PCA (Total Plate Count) (Difco Laboratories), SLB (Sodium Lactate Broth) as described by Drinan and Cogan (1992). All strains were stocked in 50% glycerol at −20° C.

Identification of *Lactobacillus plantarum* LMG P-26358

Genomic DNA was isolated from 1.5 ml of overnight MRS broth culture using a known method of Hoffman and Winston with slight modification as described by Mills S, Griffin C, Coffey A, Meijer W C, Hafkamp B, Ross R P: CRISPR Analysis of Bacteriophage Insensitive Mutants (BIMs) of Industrial *Streptococcus thermophilus*—Implications for Starter Design In submission 2009. The method of Hoffmann and Winston is disclosed in Hoffman C S, Winston F: A ten-minute DNA preparation from yeast efficiently releases autonomous plasmids for transformation of *Escherichia coli*. Gene 1987, 57:267-272.

The 16s rRNA primers CO1 (SEQ ID NO 3: AGTTTGATCCTGGCTCAG) and CO2 (SEQ ID NO 4: TACCTTGTTACGACTT) were used to amplify a product of ~1500 bp using an annealing temperature of 60° C. PCR amplification was performed in a Hybaid PCR express unit (Hybaid Ltd., Middlesex, UK) according to the manufacturer's specifications using Biotaq DNA polymerase (BioTaq, Bioline Ltd., London, UK). The PCR product was purified using a Wizard SV Gel and PCR Clean-Up System (Promega, Madison, Wis., USA) and sequenced with an automated DNA sequencer (Beckman Coulter Genomics, Hope End, Takeley, UK). The 16S rRNA gene sequence was analysed using BLAST to identify the closest bacterial neighbour, according to protocols described by S. F. Altschul et al. in Nucleic Acids Res. 1997, 25, pp. 3389-3402.

Effects of Proteinase K, pH and Temperature on the Bacteriocin Produced by *Lb. plantarum* LMG P-26358 and Stability of Production Cell-free supernatant was harvested from 1 ml of overnight culture and exposed to a final concentration of 50 mg/ml Proteinase K (Sigma-Aldrich, Poole Dorset, UK) and incubated for 2 hours at 37° C. The agar WDA was then performed against *L. innocua* with the proteinase K-treated sample and untreated cell-free supernatant as control. In order to determine the effect of pH on bacteriocin activity, the pH of cell-free supernatants was adjusted to pH values ranging from 1-10 using 1 M NaOH or 1 M HCl and incubated for 2 hours at 25° C. before performing agar WDA. In a separate experiment the effect of temperature on bacteriocin activity was assessed by incubating the cell-free supernatants at 40, 50, 60, 70, 80, 90 and 100° C. for 30 min after which activity was assessed against *L. innocua*. Stability of bacteriocin production was assessed by sub-culturing *Lb. plantarum* LMG P-26358 (2%) in MRS broth twice a day for a 10 day period and performing the agar WDA against *L. innocua* each day. All experiments were performed in triplicate.

HPLC Purification and Mass Spectrometry

The bacteriocin was purified and the molecular mass determined as follows: 50 µl of stock culture was grown overnight at 37° C. in 5 ml MRS broth. Forty ml of MRS was inoculated at 1 wt. % from the overnight culture and incubated for 6-7 hours at 37° C. and this was then used to provide a 1 wt. % inoculum for 2 litres of MRS broth. Following overnight incubation at 37° C., the culture was centrifuged at 14,160×g for 15 minutes and the supernatant discarded. Cells were mixed with 250 ml 70% isopropanol, 0.1% trifluoroacetic acid (TFA) and stirred for 3 hours at room temperature. Cells were re-centrifuged and the cell-free supernatant assayed for anti-listerial activity. The isopropanol was removed from the cell-free supernatant using a Buchi rotary evaporator (Buchi, Switzerland) and the resulting prep was passed through a 5 g, 20 ml Strata C18-E SPE column (Phenomenex, Cheshire, UK), the column was washed with 20 ml of 30% ethanol and bacteriocin was eluted with 20 ml 70% isopropanol, 0.1% TFA. Isopropanol was removed from 20 ml of the bacteriocin-containing sample and this was then applied to a C12 Proteo reverse phase HPLC column running a 25-40% acetonitrile, 0.1% TFA gradient over 35 minutes. Two HPLC runs were typically done per 2 litre prep. Mass spectrometry was performed on the anti-listerial fractions using an Axima TOF$^2$ MALDI TOF mass spectrometer (Shimadzu Biotech, Manchester, UK). A 0.5-µl aliquot of matrix solution (Sinapinic acid, 10 mg/ml in 50% acetonitrile-0.1% (v/v) TFA) was deposited onto the target and left for 5 seconds before being removed. The remaining solution was allowed air-dry and the sample solution was deposited onto the pre-coated sample spot. Matrix solution (0.5-µl) was added to the deposited sample and allowed air-dry. The sample was subsequently analysed in positive-ion linear mode. The purified peptide was resuspended in 0.1 M phosphate buffer (pH 6.8) and stored at −20° C. The activity in au/ml was determined by WDA as described previously by M. P. Ryan et al. in Appl. Environ. Microbiol. 1996, 62, pp. 612-619.

Identification of Genes Encoding the Bacteriocin Produced by *Lb. plantarum* LMG P-26358

N-terminal sequencing of the peptide was performed by Aberdeen Proteomics (Aberdeen University, Aberdeen, UK). Based on amino acid sequence similarity to plantaricin 423, primers designed to the structural gene, plaA, (423A5: SEQ ID NO 5: AAATACTATGGTAATGGGG & 423A3: SEQ ID NO 6: CATGGAAAGTGCTAATTA) as described by C. A. van Reenen et al. in Int J Food Microbiol 2003, 81, pp. 29-40. Primers designed to the whole operon in this study (423F: SEQ ID NO 7: ATGATGAAAAAAATTGAAAAA & 423R: SEQ ID NO 8: CTTGATTATGAATTAACCGT) were used for PCR amplifications. DNA was amplified in a Hybaid PCR express unit. The Expand High Fidelity PCR system (Roche Diagnostics Ltd., East Sussex, UK) was used to amplify the products according to the Roche Diagnostics applications manual. The PCR product representing the whole operon was purified using the Wizard SV Gel and PCR Clean-Up System (Promega). The purified product was cloned into the TOPO XL PCR Cloning kit (Invitrogen, Paisley, UK). Clones were sequenced with an automated DNA sequencer (Beckman Coulter Genomics, UK) using the M13-Forward and Reverse priming sites on the pCR-XL-TOPO vector. Restriction enzymes were purchased from New England Biolabs (Hertfordshire, UK) and used according to manufacturer's instructions. The sequence was annotated using ORF Finder (NCBI) and analysed using BLAST according to Altschul et al. Nucleic Acids Res. 1997, 25, pp. 3389-3402.

Mode of Action of the Bacteriocin Produced by *Lb. plantarum* LMG P-26358

To determine the mode of action of the bacteriocin produced by *Lb. plantarum* LMG P-26358 on exponential phase cells of *L. innocua*, a 2 wt. % inoculum of the culture was grown for 3 hours after which the culture was divided into two samples of equal volume. A purified preparation of the bacteriocin (2560 au/ml) was added to one sample (test) and both test and control were incubated at 37° C. for 8 hours. Optical density (600 nm) and cell numbers (colony forming units (cfu/ml)) were determined at 2 hour intervals.

In a separate experiment the mode of action of the bacteriocin produced by *Lb. plantarum* LMG P-26358 on stationary phase cells of *L. innocua* was determined. A 1 wt. % inoculum of the culture was grown overnight. The following day the cells were harvested and resuspended in 0.1 M potassium phosphate buffer (pH 7.0). The sample was then divided into test and control and 2560 au/ml of a purified preparation of the bacteriocin was added to the test. Both samples were incubated at 37° C. for 8 hours. Optical density (600 nm) and cell numbers (cfu/ml) were determined at 2 hour intervals. Each experiment was performed in triplicate and percentage killing was calculated according to the method of Deraz et al. J. Ind. Microbiol. Biotechnol 2007, 34, pp. 373-379. In particular, the following calculation was applied:

% Killing=[((initial viable cells)−(final viable cells))/(initial viable cells)]×100.

Minimum Inhibitory Concentration (MIC) and Specific Activity of the Bacteriocin Produced by *Lb. plantarum* LMG P-26358

The MIC was determined according to the method of Gravesen et al. Microbiology 2002 148, pp. 2361-2369 and Ramnath et al. Appl. Environ. Microbiol. 2000, 66, pp. 3098-3101. Briefly, 5 µl of a two-fold serial dilution of cell-free supernatant (2560 au/ml plantaricin produced by *Lb. plantarum* LMG P-26358) or purified peptide were spotted onto GM17 plates seeded with 0.25% *L. innocua*. The MIC was calculated as the minimal concentration that produced a visible zone after 18 hours at 37° C. The experiment was performed in triplicate. The specific activity was experimentally measured by generating a standard curve of bacteriocin concentration in mg/ml versus au/ml. The experiment was performed in triplicate with two different purified preparations of the bacteriocin produced by *Lb. plantarum* LMG P-26358. In both experiments the $R^2$ value was above the 95% confidence level.

Characterisation of Acid-Production by *Lactobacillus plantarum* LMG P-26358 and *Lactococcus lactis* CSK65

Cheese temperature profiles were performed as described by Harrington and Hill *Appl. Environ. Microbiol.* 1991, 57, 3405-3409. However, in the case of *Lb. plantarum* LMG P-26358, 10% RSM was supplemented with 0.1% yeast extract and 0.2 g/l $MnSO_4.4H_2O$ and the test sample was supplemented with 320 au/ml of nisin. The pH was recorded for test and control every hour for 7 hours. To test the effect of the bacteriocin produced by *Lb. plantarum* LMG P-26358 on acidification of *L. lactis* CSK65, 2560 au/ml of said bacteriocin was added to the test sample. The pH was monitored for test and control every hour for 7 hours.

Laboratory-Scale Cheese Manufacture with *Lactobacillus plantarum* LMG P-26358

Cultures were inoculated into 1 L of whole milk heated to 32° C. *L. innocua* (DPC6578) (a streptomycin resistant strain) was added to each sample vat at a level of $10^3$ cfu/ml. 30 min after inoculation Chymax rennet (Hansens, Little Island, Cork, Ireland) was added according to manufacturer's instructions and the curd was cut at the appropriate time. The temperature was then elevated from 32° C. to 38.5° C. over a 30 min period. At pH 6.2, the whey was drained and the temperature was reduced to 32° C. When the curd reached pH 5.2, the curd was further drained and pressed into moulds overnight. The cheeses were then incubated at 20° C. for 16 hours after which they were vacuum-packed and ripened at 12° C. for 4 weeks. *L. innocua* was counted in each cheese on a weekly basis by homogenising 1 g of cheese in MRD and plating serial dilutions on GM17 containing streptomycin (500 μg/ml). *Lb. plantarum* LMG P-26358 was counted by plating on LBS agar. Each cheese trial was performed in triplicate.

Industrial-Scale Gouda Cheese Manufacture with *Lactobacillus plantarum* LMG P-26358

Industrial-scale Gouda cheese was manufactured according to a standard protocol. More specifically, for each run, 1500 L of milk was used per vat to produce 15×10 kg cheese wheels with 51% fat, 41% moisture and 3% salt content. The milk was bactofugated at 68° C. for 13 sec and pasteurized at 73° C. for 13 sec, then the cheese milk was cooled down to 32° C. At this point nitrate (as 35% aqueous solution) and calcium chloride (as 33% aqueous solution) were added in the amounts of 55 and 70 gr respectively per 1500 L. Culture(s) combination(s) were added as indicated below under the heading "Gouda Cheese Production on industrial scale using *Lactobacillus plantarum* LMG P-26358 as an Adjunct Culture." An amount of calf rennet, Ceska®-Lase 150 IMCU (CSK Food Enrichment, Ede, The Netherlands) added was 20 gram per 1500 L cheese milk. After a coagulation time of 35 min, the curd was cut for 20 min and then 40% of the whey was removed. The remaining lactose was washed out of the curd by adding hot water. The curd was further stirred for 33 min at a constant temperature of 35° C. After whey drainage, the cheese was pressed for 90 min and brined for 72 hours. The pH of the cheeses after one day was 5.20. The cheeses were coated multiple times at regular intervals with Ceska®-Coat during 18 weeks of ripening at 13° C.

The industrial cheeses thus produced were assayed for antimicrobial activity by homogenising 1 g of cheese in 9 mL of diluent to which $10^4$ cfu/ml of *L. innocua* (DPC6578) was added from an overnight culture. A control was also set up which did not contain any cheese. The cheese/*Listeria* slurry was then incubated at room temperature over 24 hours and *Listeria* counts were determined at 5 and/or 24 hours by plating serial dilutions on GM17 agar containing streptomycin (500 μg/ml). A plug of each cheese was also overlaid with *L. innocua* to determine if bacteriocin produced by *Lb. plantarum* LMG P-26358 was active. Analysis was performed in triplicate on days 1 and 14 and weeks 6, 13 and 18.

Detection of Nisin and Plantaricin 423 in Industrial Cheeses by MALDI-TOF Mass Spectrometry Cheese samples were subjected to mass spectrometry to detect the presence of bacteriocins. Briefly, 20 ml of 70% isopropanol, 0.1% TFA was added to 1 g of cheese sample and mixed at room temperature for 3-4 hours. Cheese mixtures were centrifuged and 20 ml of 70% isopropanol, 0.1% TFA was added to the supernatant. The isopropanol was removed using rotary evaporation and suspensions were re-centrifuged to spin down particulate matter. The pH of the supernatant was adjusted to 4-5 by adding approximately 30 μl of 7.5 N NaOH and then passed through a 5 g 20 ml Phenomenex Strata C18-E SPE column, columns were washed with 20% ethanol and bacteriocins eluted with 70% isopropanol, 0.1% TFA. The isopropanol was removed from the 70% isopropanol, 0.1% TFA samples before applying to a semi prep C12 Proteo Jupiter RP-HPLC column running a 25-48% acetonitrile, 0.1% TFA gradient over 35 minutes. Eluent was monitored via UV at 214 nm. Fractions were collected at 1 min intervals and nisin- and plantaricin-containing fractions were analysed by MALDI-TOF mass spectrometry as previously described to confirm their presence.

Spray-Drying

*Lb. plantarum* LMG P-26358 was grown to 8 l in 20% RSM (reconstituted skim milk) with 0.5% yeast extract and 0.2 g/l $MnSO_4.4H_2O$. The fermentate was concentrated to 40% total solids in a single-effect falling-film evaporator (Anhydro F1-Lab) before spray-drying. Concentrates were then dehydrated in a pilot-scale Anhydro spray drier (Model Lab 3) at an inlet temperature of 187° C. and an air outlet temperature of ~85° C. The powder was assayed for viable cells by plating on PCA and LBS, and counts were compared across both sets of plates to determine the cfu of *Lb. plantarum* LMG P-26358 per g of spray dried powder. Anti-listerial activity was assessed by adding the powder at 1% (w/v), 5% (w/v), 10% (w/v) and 15% (w/v) to $10^4$ cfu/ml of *L. innocua* (DPC6578) in GM17 broth (Difco Laboratories). The culture/powder mix was incubated for 6 hours at 37° C. and samples were removed every 2 hours to count *Listeria* by selecting on GM17 with streptomycin (500 μg/ml). Each experiment was performed in triplicate.

Antifungal Assays

Fungal contaminants on laboratory-scale cheeses were streaked onto PDA (Potato Dextrose agar) (Difco Laboratories) and YGC (Yeast extract, Glucose, Chloramphenicol agar) (Difco Laboratories). The plates were incubated for 5 days at 25° C. Growth on the plates was examined for different morphologies. Spores and yeast cells were removed with a sterile loop and streaked onto PDA and YGC, respectively, to purify the fungal contaminants. Yeasts and mounds were then stocked on YGC and PDA slants and stored at 4° C. following growth. The antifungal activity assay was performed essentially as described by Magnusson and Schnurer Appl. Environ. Microbiol. 2001, 67, pp. 1-5. Streaks of *Lb. plantarum* LMG P-26358 of approximately 2 cm were grown for 48 hours on MRS agar and were then overlaid with 10 ml of PDA (0.7% agar) or YGC (0.7% agar) containing $10^4$ fungal spores or yeast cells, respectively. The plates were then incubated aerobically at 30° C. for a further 48 hours after which they were examined for clear zones of inhibition around the streaks.

Results

Isolation and Identification of *Lactobacillus plantarum* LMG P-26358

*Lb. plantarum* was isolated from a soft French artisanal cheese due to its associated production of a large zone from the colony when overlaid with *L. innocua*. Following purification it was later identified as *Lb. plantarum* by 16s rRNA gene sequencing and designated and deposited at BCCM as *Lb. plantarum* LMG P-26358. The sequence as determined is shown in scheme 1. To determine if the inhibitory activity was protein in nature, the supernatant was treated with proteinase K and tested against *L. innocua* by WDA. The loss of activity confirmed that the antimicrobial substance produced by *Lb. plantarum* was indeed proteinaceous. The level of inhibitory activity in sulture supernatant against *L. innocua* was determined to be 2560 au/ml (~7-8 mm zone) when measured by WDA. Sugar acidification profiles indicated that *Lb. plantarum* LMG P-26358 can grow efficiently on both glucose and lactose with generation times (GTs) of 100 mins and specific growth rates of 0.1814 and 0.1815, respectively. The strain of *Lb. plantarum* LMG P-26358 is also capable of growing on sucrose, trehalose, fructose, galactose, maltose and cellobiose. Maltose was the most efficient sugar for growth with a GT of 79 mins and specific growth rate of 0.2277, while the strain was unable to metabolise raffinose. See also Table 4.

Identification of the Antimicrobial Substance Produced by *Lactobacillus plantarum* LMG P-26358 and Characterisation of the Genetic Machinery The antimicrobial substance was purified by HPLC and the molecular mass was determined to be 3929 Da using MALDI-TOF mass spectrometry. The peptide was then partially sequenced revealing the first 10 amino acids. These 10 amino acids were found to be homologous to the class IIa bacteriocin plantaricin 423 which is produced by *Lb. plantarum* 423 and has a molecular mass of 3932.74 (Van Reenen et al., 2003). Based on the sequence of plantaricin 423 primers were generated to the bacteriocin structural gene and to the complete operon involved in the production of the bacteriocin. Both sets of primers generated PCR products of the correct size for the structural gene (150 bps) and the operon (~3582 bps). DNA sequence analysis and annotation of the amplified operon revealed that the structural gene was identical to that of plantaricin 423. While 17 base pair differences were observed across the remainder of the operon, such changes could be considered silent in the majority of cases. The bacteriocin produced by *Lb. plantarum* LMG P-26358 is thus a plantaricin, the peptide sequence of which matches the structure and amino acid sequence of plantaricin 423. Overall, four genes are encoded on the plantaricin operon of *Lb. plantarum* LMG P-26358 which is usual for class IIa bacteriocins. The first gene plaP26358 encodes the pre-bacteriocin. The presequence is 58 bp in length and is cleaved at the C-terminal side of the double glycine motif (GG) to release the mature peptide. PlaB encodes the immunity gene, plaC encodes an accessory protein of unknown function and plaD encodes the ABC (ATP-binding cassette) transporter which is required for secretion of the bacteriocin. As plantaricin 423 contains a disulfide bridge in both the N-terminal and C-terminal domains, the bacteriocin produced by *Lb. plantarum* LMG P-26358, with an identical peptide sequence, presumably contains two such bridges.

Effect of Heat and pH on the Activity of the Bacteriocin Produced by *Lb. plantarum* LMG P-26358 and Stability of Bacteriocin Production by *Lb. plantarum* LMG P-26358 Over a 10 Day Period Heat treatment of the bacteriocin at 40, 50, 60, 70, 80, 90 and 100° C. for 30 minutes did not compromise its antimicrobial activity. Likewise, the activity of the bacteriocin was unaffected by pH as the bacteriocin continued to produce 2560 au/ml following incubation of the supernatant at pH values from 1-10 for 2 hours at 25° C. The producing strain, *Lb plantarum* LMG P-26358, was sub-cultured for 10 days and the supernatant was assayed for activity each day. The strain continued to produce equivalent potent activity against *L. innocua* on each day of the 10-day period.

Spectrum of Inhibition

The activity of the bacteriocin produced by *Lb. plantarum* LMG P-26358 was assayed against 26 indicator strains (Table 1) which included LAB starters such as *Lactococcus lactis* and *Lactobacillus* species as well as food spoilage and pathogenic bacteria such as *Bacillus subtilis* and *Salmonella typhi*. Apart from the expected inhibitory activity against *L. innocua*, the bacteriocin produced by *Lb. plantarum* LMG P-26358 also inhibited *E. faecalis*, producing a 5 mm zone, and *Enterococcus faecium*, producing a 2 mm zone. The lack of inhibition against the starters tested in the study indicates that *Lb. plantarum* LMG P-26358 is a suitable adjunct for cheese manufacture.

Mode of Action of the Bacteriocin Produced by *Lb. plantarum* LMG P-26358

The effect of the bacteriocin produced by *Lb. plantarum* LMG P-26358 on *Listeria* was investigated to determine if it has a bactericidal or bacteriostatic mode of action using both exponential and stationary phase cells. The purified peptide (resuspended in phosphate buffer) with an initial activity of 102,400 au/ml was added to cell suspensions (either exponential or stationary phase) at a final concentration of 2560 au/ml and growth was assessed by measuring the optical density and cell numbers over an eight hour period, and percentage killing was also calculated. Over the eight hour period, a marked decrease was observed in both optical density and cell viability for exponential and stationary phase cells when compared to controls (Table 2). Within the first two hours a three-log reduction in *Listeria* numbers was observed for exponential phase cells in the presence of the bacteriocin produced by *Lb. plantarum* LMG P-26358 corresponding to a 99.9% reduction. After 4 hours the reduction increased to 100% (5 log reduction), while after 6 and 8 hours, a three-log reduction in cell viability was observed corresponding to ~99.9% killing. The optical density decreased dramatically within the eight hour period for exponential cells in the presence of the bacteriocin produced by *Lb. plantarum* LMG P-26358 indicating that the activity of the bacteriocin against exponential cells is bactericidal with simultaneous lysis. A similar pattern was observed for stationary phase cells. Indeed, a three log reduction was recorded for cells in the presence of bacteriocin within the first 2 hours, corresponding to 99.9% killing and a 2 log reduction was observed after the eighth hour (99% killing). The dramatic decrease in optical density indicates that the bacteriocin produced by *Lb. plantarum* LMG P-26358 also has a bactericidal effect on stationary phase cells of *L. innocua*.

Minimum Inhibitory Concentration and Specific Activity of the Bacteriocin Produced by *Lb. plantarum* LMG P-26358

The minimum inhibitory concentration (MIC), determined as the minimal concentration showing a visible zone of inhibition, against *L. innocua* was estimated to be 40 au/ml using purified bacteriocin produced by *Lb. plantarum* LMG P-26358 or cell-free supernatant. A standard curve was generated to determine specific activity of the plantaricin. The data points could be fitted ($R^2$=0.9896) to the equation $y=10^{-5}(X)$ where X is the activity expressed as au/ml and y is the activity expressed as mg/ml. Therefore, the MIC which was determined to be 40 au/ml is equivalent to 0.4 µg/ml (0.10173 µM).

On a separate notice, it was found that under the same test conditions, bacteriocin produced by *Lb. plantarum* LMG P-26358 has the same MIC against a plurality of species of *Listeria monocytogenes*, including *L. monocytogenes* DPC3440 (Scott A).

Ability of *Lactobacillus plantarum* LMG P-26358 to Survive in a Dairy Environment with Nisin-Producing Starters and Efficacy of Nisin Producers in the Presence of *Lactobacillus plantarum* LMG P-26358

*Lb. plantarum* LMG P-26358 was found to grow adequately in 10% RSM substituted with 0.1% yeast extract.

Supplementation of the starter culture medium with 0.2 g/l MnSO$_4$.4H$_2$O was also shown to facilitate its growth. Combining the strain with the nisin producer L. lactis CSK 65 (produces 320 au/ml of nisin) eliminated the requirement for yeast extract addition to 10% RSM (result not shown) and the strain continues to produce bacteriocin. Lb. plantarum LMG P-26358 was then grown in 10% RSM, 0.1% yeast extract and 0.2 g/l MnSO$_4$.4H$_2$O in the absence and presence of 320 au/ml of nisin (purified from Nisaplin®), and cell counts and bacteriocin production were analysed after 4, 8 and 24 hours. The presence of nisin inhibited the growth of Lb. plantarum LMG P-26358 to some extent (Table 3a). Indeed, after four hours, the strain grown with nisin was approximately 100 fold less than the control ($1.73 \times 10^6$ cfu/ml versus $1.13 \times 10^8$ cfu/ml, respectively) and the zone sizes against Listeria were recorded at 4 mm (strain with nisin) versus 6 mm (control), respectively. By the eighth hour only a 10 fold difference existed between test ($1.66 \times 10^7$ cfu/ml) and control ($4.6 \times 10^8$ cfu/ml), although the control strain produced a larger zone of ~8.5 mm against Listeria while the test strain produced a zone of only 4.5 mm. After 24 hours both test and control produced a zone of 8.5 mm against Listeria although the control was 10 fold cfu/ml higher ($3.3 \times 10^9$ cfu/ml) than the strain grown in the presence of nisin ($5 \times 10^8$ cfu/ml).

The effect of the bacteriocin produced by Lb. plantarum LMG P-26358 on nisin production was evaluated by examining cell viability and nisin production (using the indicator organism L. lactis HP) following growth of L. lactis CSK65 in the presence and absence of 2560 au/ml of the bacteriocin produced by Lb. plantarum LMG P-26358 (Table 3b). Antimicrobial activity against L. lactis HP did not differ between test and control over the 24 hour period. However, cell numbers were slightly lower for the strain grown in the presence of the bacteriocin produced by Lb. plantarum LMG P-26358, which were 10 fold lower than the control at 4 and 24 hours. In terms of acidification, the presence of 2560 au/ml of the bacteriocin produced by Lb. plantarum LMG P-26358 did not alter the acidifying properties of L. lactis CSK65 (data not shown). However, the acidification properties of Lb. plantarum LMG P-26358 were severely reduced in the presence of 320 au/ml of nisin. To be more precise, whereas in the absence of nisin the strain Lb. plantarum LMG P-26358 was capable of reducing the pH of the reconstituted skim milk from 6.4 to 5.8 within 6 hours and to below 5.5 within 7 hours, in the presence of 320 IU/ml of nisin the same strain was not capable of reducing the pH of the reconstituted skim milk from 6.4 to 6.2 or below, over the same time span.

Laboratory-Scale Cheese Production Using Lactobacillus plantarum LMG P-26358 as an Adjunct Culture Laboratory-scale cheese spiked with $10^3$ cfu/ml of L. innocua was manufactured to test the anti-listerial capacity of Lb. plantarum LMG P-26358 in the presence and absence of the nisin producer L. lactis CSK65. Four vats were set up as follows, percentages as volume/volume:
Vat 1=0.75% L. lactis DPC4268 (cheese starter); Vat 2=0.75% L. lactis DPC4268, 0.75% L. lactis CSK65 (nisin producer); Vat 3=0.75% L. lactis DPC4268, 0.75% Lb. plantarum LMG P-26358; Vat 4=0.75% L. lactis DPC4268, 0.5% Lb. plantarum LMG P-26358, 0.5% L. lactis CSK65.

Each culture was provided as a freshly grown overnight culture. It is noted the fresh culture of L. lactis CSK65 may be replaced with similar effect by another suitable freshly grown lactococcal nisin-producing culture such as a fresh culture of L. lactis subsp. lactis BS-10 ex. Chr. Hansen A/S, Denmark, or a fresh culture of L. lactis subsp. lactis biovar diacetylactis UL719 as described in Bouksaim et al. International Journal of Food Microbiology 2000, 59(3), pp. 141-156.

Each cheese was ripened at 12° C. for 4 weeks and Listeria and Lb. plantarum LMG P-26358 was enumerated each week of the ripening period. On day 28 a plug of each cheese was also overlaid with L. innocua to determine if the bacteriocin was still active. By day 28, L. innocua numbers were dramatically reduced in Vat 3 as compared to Vats 1 and 2 and Listeria was not detected in Vat 4 suggesting that the combination of the bacteriocin produced by Lb. plantarum LMG P-26358 and nisin was more effective than the bacteriocin produced by Lb. plantarum LMG P-26358 alone. Lb. plantarum LMG P-26358 was present at $10^8$ cfu/ml on days 1 and 28 after cheese manufacture. Overlays of cheese plugs on day 28 indicated that the Lb. plantarum LMG P-26358 containing cheeses produced a zone of inhibition against L. innocua.

In another experiment, laboratory-scale Gouda Cheese was manufactured to determine the anti-listerial activity of Lb. plantarum LMG P-26358 using a 0.4% inoculum of the culture in combination with a nisin producer. However, in this case, the antimicrobial effect was much less (results not shown). Counts of Lb. plantarum LMG P-26358 reached only $10^7$ cfu/ml on the day of cheese manufacture and remained at this level throughout the 28 day ripening period, which may be a reflection of the smaller inoculum. We have already observed that at $10^7$ cu/ml, Lb. plantarum LMG P-26358 is not as active against Listeria, producing a much smaller zone of inhibition when measured by WDA (Table 3a).

Gouda Cheese Production on Industrial Scale Using Lactobacillus plantarum LMG P-26358 as an Adjunct Culture 12 kg Gouda cheese wheels were manufactured in four different cheese vats according to the industrial protocol indicated above, under the heading "Industrial-scale Gouda cheese manufacture with Lactobacillus plantarum LMG P-26358."

Regarding the bacterial cultures, the cheese vats were set up as follows.
Vat 1: 375 g of culture D509 was added per 1500 litres of cheese milk, and Gouda cheese was produced according to said known protocol. D509 is a mixed culture concentrate in the form of frozen pellets comprising equal weight amounts of a nisin-immune strain of L. lactis subsp. cremoris 13M and a nisin-producing strain of L. lactis biovar diacetylactis TC17-5, each at about $1.10^{10}$ cfu/ml. The total viable cell count in D509 is about $1.10^{10}$ cfu/ml. D509 is commercially available, for example supplied in 500 ml gable tops, from CSK Food Enrichment BV, Leeuwarden, The Netherlands.
Vat 2: 278 g of a nisin-immune culture (C76) and 700 g of ZC-LMG P-26358 were added per 1500 litres of cheese milk, and Gouda cheese was produced according to the same protocol. Herein, C76-5 is a culture concentrate in the form of frozen pellets, comprising L. lactis subsp. cremoris 13M at $1.10^{10}$ cfu/ml. C76-5 can be obtained from CSK Food Enrichment, Leeuwarden, the Netherlands. ZC-LMG P-26358 is a concentrate of Lb. plantarum LMG P-26358 in the form of frozen pellets. This was obtained by culturing LMG P-26358 under anaerobic conditions in a fermentor as follows: 20 ml of liquid medium of MRS broth was inoculated with LMG P-26358 for 16 h at 37° C. until pH 6.9. The culture was then centrifuged for 10-15 minutes at 4400 rpm (17° C.). To the obtained concentrate, lactose was added as a cryoprotector (8%). This concentrate was frozen in liquid nitrogen to obtain ZC-LMG P-26358 as pellets having a diameter of between 0.01 and 0.5 cm. The viable cell count of LMG P-26358 in these pellets was $2.10^{10}$ cfu/ml (counting on MRS agar comprising 0.2 g/l of $MnSO_4.4H_2O$).

Vat 3: 375 g of culture D509 in combination with 700 g of ZC-LMG P-26358 was added per 1500 litres of cheese milk, and Gouda cheese was produced according to the same protocol. Herein, ZC-LMG P-26358 is the concentrate of *Lb. plantarum* LMG P-26358 in the form of frozen pellets described above.

Vat 4: 375 g of culture D509 in combination with 1400 g of ZC-LMG P-26358 was added per 1500 litres of cheese milk, and Gouda cheese was produced according to the same protocol. Herein, ZC-LMG P-26358 is the concentrate of *Lb. plantarum* LMG P-26358 in the form of frozen pellets described above.

The cheese wheels were ripened, whilst receiving several layers of Ceska-Coat® at regular intervals, at 13° C. and at a relative humidity of between 83-89% RH according to a conventional protocol for 18 weeks. The cheeses were tested over this 18 week period for anti-listerial activity by generating cheese/*Listeria* slurries in MRD. The results are summarised in Table 5. The cheeses produced with *Lb. plantarum* LMG P-26358 were much more effective at controlling *Listeria* numbers than using the nisin producer alone. A slight antagonistic effect may have occurred between the nisin producer and *Lb. plantarum* LMG P-26358 as zones from cheese plugs of Vats 3 and 4 were always slightly smaller than zones from Vat 2. We have already observed that nisin does slow the growth of *Lb. plantarum* LMG P-26358 (Table 3). However each of the cheeses offered a level of protection against *Listeria* during the ripening period. Indeed nisin and the bacteriocin produced by *Lb. plantarum* LMG P-26358 were both detected in the appropriate cheeses by mass spectrometry over the 18 week ripening period.

Interestingly and importantly, after ripening for 18 weeks, the cheeses of Vat 2 had developed an unpleasant sulphury-type off flavour. This off-flavour was much reduced or even absent in the cheese produced in vats 3 or 4, i.e. in the presence of a nisin-producing strain.

It is noted that in Vat 2, the nisin-immune culture C76 can be replaced, with similar results, by any suitable lactococcal acidifying culture since no nisin-producing culture is present. For example, C76 can be replaced by R-604 in F-DVS form, ex Chr. Hansen A/S, Denmark.

The trial was successfully repeated wherein to each cheese vat, 187.5 g of culture L700 was further added per 1500 litre of cheese milk. L700 is a debittering culture comprising thermophilic lactobacilli, especially of *Lb. helveticus*, supplied by CSK Food Enrichment BV, The Netherlands. The taste of the cheese was found to be further improved by the addition of L700.

Frequency of Bacteriocin Resistance Development in *Listeria innocua*

The frequency of development of resistance in *L. innocua* to 2560 au/ml of the bacteriocin produced by *Lb. plantarum* LMG P-26358 (purified preparation) was calculated at $1.13 \times 10^{-3}$. However, the frequency of resistance development against 320 au/ml nisin was lower at $2.16 \times 10^{-2}$. Simultaneous exposure to the bacteriocin produced by *Lb. plantarum* LMG P-26358 and nisin at the above levels reduced the frequency of resistance development to $1.34 \times 10^{-4}$. The resistant colonies were picked off and tested for their sensitivity to the bacteriocin produced by *Lb. plantarum* LMG P-26358. However, all bacteriocin resistant strains remained sensitive to 2560 au/ml of the bacteriocin produced by *Lb. plantarum* LMG P-26358 suggesting that the cells were 'tolerant' rather than completely resistant.

Antimicrobial Activity of Spray-Dried Powder of *Lb. plantarum* LMG P-26358

A total of 8 l of an overnight fermentate of *Lb. plantarum* LMG P-26358 was spray-dried, yielding approximately 1 kg of powder containing $6.0 \times 10^4$ viable cfu/g of *Lb. plantarum* LMG P-26358. The powder was tested against *L. innocua* at concentrations of 1, 5, 10 and 15%. All concentrations tested exhibited antimicrobial activity against *L. innocua*. Indeed, at 15% the powder reduced *Listeria* numbers by approximately 4 logs within 6 hours when compared with the control.

Anti-Fungal Activity of *Lactobacillus plantarum* LMG P-26358

We observed that laboratory-scale Cheddar cheeses manufactured with *Lb. plantarum* LMG P-26358 were less susceptible to yeast and mould contamination. The fungal contaminants were isolated from contaminated cheeses and consisted of yeast, green mould and white mould. Two cm streaks of *Lb. plantarum* LMG P-26358 were overlaid with each of the three fungal contaminants. The white mould was found to be particularly susceptible to *Lb. plantarum* LMG P-26358.

In the examples above, the commercially available nisin-producing strain CSK65 (ex CSK Food Enrichment BV) can also be applied as a single-strain acidifying starter culture for cheese. CSK65 is capable of lowering the pH of sterilised milk from a value of about 6.5-6.7 at t=0 to a value of pH=5 after 8 hours' fermentation of the milk at 30° C., said milk being inoculated with 1% of an overnight culture of CSK65.

TABLE 1

Inhibition Spectra of *Lactobacillus plantarum* LMG P-26358

| Indicator strain | Medium | Temp | Sensitivity |
|---|---|---|---|
| *Bacillus cereus* DPC 6085/6086 | BHI | 37° C. | — |
| *Bacillus subtilus* DPC 6511 | BHI | 37° C. | — |
| *Enterococcus faecalis* DPC 5055/LMG 7973 | BHI | 37° C. | 5 mm zone |
| *Enterococcus faecium* DPC 5056** | BHI | 37° C. | 2 mm zone |
| *E. coli* P1432- DPC 6054 | BHI | 37° C. | — |
| *Salmonella typhi* | TSA/BHI | 37° C. | — |
| *Clostridium sporogenes* DPC 6341* | RCM | 37° C. | — |
| *Clostridium tyrobutyricum* DPC 6342* | RCM | 37° C. | — |
| *Lactobacillus casei* DPC 6125* | MRS | 30° C. | — |
| *Lactobacillus acidophilus* DPC 5378* | MRS | 37° C. | — |
| *Lactobacillus delbreukii* subsp. *delbreukii* DPC 5385* | MRS | 37° C. | — |
| *Lactobacillus delbreukii* subsp. *lactis* DPC 5387* | MRS | 30° C. | — |
| *Lactobacillus delbreukii* subsp. *bulgaricus* DPC5383* | MRS | 30° C. | — |

TABLE 1-continued

Inhibition Spectra of *Lactobacillus plantarum* LMG P-26358

| Indicator strain | Medium | Temp | Sensitivity |
|---|---|---|---|
| *Lactobacillus helveticus* DPC4571* | MRS | 37° C. | — |
| *Lactococcus lactis* subsp. *lactis* biovar *diacetylactis* CSK1411 | LM17 | 35° C. | — |
| *Lactococcus lactis* subsp. *lactis* biovar *diacetylactis* CSK1412 | LM17 | 35° C. | — |
| *Lactococcus lactis* subsp. *lactis* biovar *diacetylactis* CSK1413 | LM17 | 35° C. | — |
| *Lactococcus lactis* subsp. *cremoris* HP DPC 5718 | LM17 | 30° C. | — |
| *Lactococcus lactis* subsp. *lactis* DPC 4268 | LM17 | 30° C. | — |
| *Lactococcus lactis* subsp. *cremoris* MG1614 (pLP712) | LM17 | 30° C. | — |
| *Lactococcus lactis* subsp. *cremoris* CSK 2775 | LM17 | 30° C. | — |
| *Leuconoctos lactis* DPC 3838 | MRS | 30° C. | — |
| *Listeria innocua* | GM17 | 37° C. | 7 mm zone |
| *Propionibacterium* CSK 912* | SLB | 30° C. | — |
| *Propionibacterium* CSK 921* | SLB | 30° C. | — |
| *Propionibacterium* CSK 1196* | SLB | 30° C. | — |
| *Listeria monocytogenes* DPC6180 | GM17 | 37° C. | 7 mm zone |
| *Listeria monocytogenes* DPC3440 (Scott A) | GM17 | 37° C. | 7 mm zone |

*= Anaerobe
**= Facultative anaerobe

TABLE 2

Mode of Action of Plantaricin Produced by *Lb. plantarum* LMG P-26358

| Time (h) | Control (cfu/ml) | 2560 au/ml Plantaricin | % Killing |
|---|---|---|---|
| Stationary Phase Cells | | | |
| 2 | $2.23 \times 10^9$ | $2.47 \times 10^6$ | 99.9 |
| 4 | $1.07 \times 10^9$ | $2.57 \times 10^6$ | 99.8 |
| 6 | $1.03 \times 10^9$ | $7.00 \times 10^6$ | 99.3 |
| 8 | $6.67 \times 10^8$ | $8.67 \times 10^6$ | 98.7 |
| Exponential Phase Cells | | | |
| 2 | $9.33 \times 10^8$ | $3.00 \times 10^5$ | 99.97 |
| 4 | $1.80 \times 10^9$ | $8.33 \times 10^4$ | 100.00 |
| 6 | $2.80 \times 10^9$ | $3.00 \times 10^6$ | 99.89 |
| 8 | $2.90 \times 10^9$ | $7.67 \times 10^6$ | 99.74 |

TABLE 3(a)

Performance of *Lactobacillus plantarum* LMG P-26358 in Presence and Absence of Nisin in 10% RSM, 0.1% Yeast Extract and 0.2 g/L MnSO$_4$•4H$_2$O

| | *Lb. plantarum* LMG P-26358 | | *Lb. plantarum* LMG P-26358 & Nisin (320 au/ml) | |
|---|---|---|---|---|
| Time (h) | Cfu/ml | Zone Size$^a$ | Cfu/ml | Zone Size$^a$ |
| 4 | $1.13 \times 10^8$ | 6 mm | $1.73 \times 10^6$ | 4 mm |
| 8 | $4.6 \times 10^8$ | 8.5 mm | $1.66 \times 10^7$ | 4.5 mm |
| 24 | $3.3 \times 10^9$ | 8.5 mm | $5.0 \times 10^8$ | 8.5 mm |

TABLE 3(b)

Performance of *Lactococcus lactis* CSK65 in presence and absence of the plantaricin produced by *Lb. plantarum* LMG P-26358

| | *L. lactis* CSK65 | | *L. lactis* CSK65 & plantaricin produced by *Lb. plantarum* LMG P-26358 (2650 au/ml) | |
|---|---|---|---|---|
| Time (h) | Cfu/ml | Zone Size$^b$ | Cfu/ml | Zone Size$^b$ |
| 4 | $5.49 \times 10^7$ | 6 mm | $8.6 \times 10^6$ | 5 mm |
| 8 | $5.15 \times 10^7$ | 6 mm | $1.23 \times 10^7$ | 5 mm |
| 24 | $1.8 \times 10^8$ | 5 mm | $5.3 \times 10^7$ | 5 mm |

$^a$Zone size against *L. innocua*;
$^b$Zone size against *L. lactis* HP

TABLE 4

Growth profile of *Lactobacillus plantarum* LMG P-26358 in MRS broth substituted with various sugars. Generation time (GT) and specific growth rate (µmax) is calculated for *Lb. plantarum* LMG P-26358 in the presence of each sugar. µmax is determined as the maximum slope in the OD$_{600}$ vs. time curve representing growth of the *Lb. plantarum* LMG P-26358 in the MRS broth.

| Sugar | Concentration of sugar in the MRS broth | GT/min | µmax/ OD$_{600}$ · hour$^{-1}$ |
|---|---|---|---|
| Glucose | 0.5% | 103 | 0.1761 |
| Glucose | 2% | 100 | 0.1814 |
| Lactose | 2% | 100 | 0.1815 |
| Sucrose | 2% | 86 | 0.2088 |
| Trehalose | 2% | 92 | 0.1963 |
| Fructose | 2% | 104 | 0.174 |
| Galactose | 2% | 123 | 0.1473 |
| Maltose | 2% | 79 | 0.2277 |
| Raffinose | 2% | 246 | 0.0734 |
| Cellobiose | 2% | 90 | 0.2018 |
| Negative reference (no sugar) | Negative reference (no sugar) | 225 | 0.0804 |

TABLE 5

*Listeria innocua* counts following 5 or 24 hours of exposure to ~1 g of industrial cheeses; Vat 1 = mixed culture D509; Vat 2 = nisin-immune *L. lactis* C76 in combination with a concentrated culture of *Lb. plantarum* LMG P-26358; Vat 3 = mixed culture D509 in combination with a concentrated culture of *Lb. plantarum* LMG P-26358; Vat 4 = as Vat 3 with the double amount of the concentrated culture of *Lb. plantarum* LMG P-26358.

| | *Listeria innocua* (cfu/ml) after exposure to 1 g of cheese | | | | | |
|---|---|---|---|---|---|---|
| Vat No. | Day 1: 5 h | Day 14: 5 h | Week 6: 5 h | Week 13: 5 h | Week 18: 5 h | Week 18: 24 h |
| Vat 1 | $4.48 \times 10^4$ | $9.06 \times 10^5$ | $4.62 \times 10^5$ | $3.61 \times 10^5$ | $5.80 \times 10^5$ | $9.82 \times 10^5$ |
| Vat 2 | $1.10 \times 10^4$ | $6.69 \times 10^4$ | $2.72 \times 10^4$ | $8.57 \times 10^3$ | $8.70 \times 10^4$ | $1.88 \times 10^4$ |
| Vat 3 | $2.93 \times 10^4$ | $9.40 \times 10^4$ | $4.63 \times 10^4$ | $3.36 \times 10^4$ | $8.80 \times 10^4$ | $6.19 \times 10^4$ |
| Vat 4 | $1.96 \times 10^4$ | $1.72 \times 10^5$ | $2.60 \times 10^4$ | $8.14 \times 10^4$ | $6.05 \times 10^4$ | $4.02 \times 10^4$ |
| Control | $8.00 \times 10^5$ | $3.78 \times 10^6$ | $8.00 \times 10^5$ | $1.30 \times 10^8$ | $3.30 \times 10^5$ | $5.71 \times 10^6$ |

Scheme 1. 16S rRNA gene sequence of isolated strain deposited at BCCM as LMGP-26358

TGAGTGGCGAACTGGTGAGTAACACGTGGGAAACCTGCCCAGAAGCGGGG

GATAACACCTGGAAACAGATGCTAATACCGCATAACAACTTGGACCGCAT

GGTCCGAGNTTGAAAGATGGCTTCGGCTATCACTTTTGGATGGTCCCGCG

GCGTATTAGCTAGATGGTGGGGTAACGGCTCACCATGGCAATGATACGTA

GCCGACCTGAGAGGGTAATCGGCCACATTGGGACTGAGACACGGCCCAAA

CTCCTACGGGAGGCAGCAGTAGGGAATCTTCCACAATGGACGAAAGTCTG

ATGGAGCAACGCCGCGTGAGTGAAGAAGGGTTTCGGCTCGTAAAACTCTG

TTGTTAAAGAAGAACATATCTGAGAGTAACTGTTCAGGTATTGACNGGTA

TTTAACCAGAAAGCCACGGCTAACTACGTGCCAGCAGCCGCGGTAATACG

TAGGTGGCAAGCGTTGTCCGGATTTATTGGGCGTAAAGCGAGCGCAGGCG

GTTTTTTAAGTCTGATGTGAAAGCCTTCGGCTCAACCGAAAAAGTGCATC

GGAAACTGGGAAACTT

The invention claimed is:

1. A freeze-dried or frozen mixed lactic acid bacterial culture composition comprising:
   (a) one or more strains of lactic acid bacteria capable of producing a Class IIa type bacteriocin, wherein at least one of the strains is *Lactobacillus* spp.; and
   (b) one or more strains of lactic acid bacteria capable of producing a Class I type bacteriocin, wherein at least one of the strains of lactic acid bacteria capable of producing a Class I type bacteriocin is selected from the group consisting of *Lactococcus* spp; and
   (c) optionally, one or more further lactic acid bacterial strains; and
   (d) one or more additives present in an amount up to 20 wt. % relative to the weight of the composition.

2. The mixed lactic acid bacterial culture composition according to claim 1, wherein:
   (A) at least one or more of the strains of lactic acid bacteria capable of producing a Class IIa type bacteriocin is:
      (i) a strain of *Lb. plantarum*,
      (ii) a strain having a 16S rRNA gene with a sequence that has more than 97% similarity with SEQ ID NO 1,
      (iii) *Lb. plantarum* deposited under number LMG P-26358, or
      (iv) a mutant of *Lb. plantarum* (LMG P-26358) which has the capability to produce the same Class IIa type bacteriocin and has 100% 16S rRNA gene similarity with SEQ ID NO 1, and/or wherein at least one or more of the lactic acid bacteria capable of producing a Class I type bacteriocin is a lactic acid bacterial strain which is capable of producing a nisin; or
   (B) at least one or more of the lactic acid bacteria capable of producing a Class I type bacteriocin is a lactic acid bacterial strain which is capable of producing a nisin and at least one or more of the strains of lactic acid bacteria capable of producing a Class IIa type bacteriocin is not capable of growing in the presence of the nisin at a concentration of at least 300 IU/mL.

3. The mixed lactic acid bacterial culture composition according to claim 1, wherein the one or more strains of lactic acid bacteria capable of producing a Class IIa type bacteriocin are present in the composition at a total viable cell count of at least $1 \times 10^8$, and wherein the one or more strains of lactic acid bacteria capable of producing a Class I type bacteriocin are present in the composition at a total viable cell count of at least $1 \times 10^8$.

4. The mixed lactic acid bacterial culture composition according to claim 1, wherein the one or more strains of lactic acid bacteria capable of producing a Class IIa type bacteriocin comprises the strain of *Lb. plantarum* deposited under number LMG P-26358, or a mutant thereof which has the capability to produce a Class IIa type bacteriocin and has 100% 16S rRNA gene similarity with LMG P-26358.

5. The mixed lactic acid bacterial culture composition according to claim 1, wherein the one or more strains of lactic acid bacteria capable of producing a Class I type bacteriocin is selected from *L. lactis ssp. lactis biovar. diacetylactis*, the strains being capable of producing a nisin.

6. The mixed lactic acid bacterial culture composition according to claim 1, wherein the composition is in frozen form.

7. The mixed lactic acid bacterial culture composition according to claim 6, wherein the composition is in the form of frozen particles having a diameter of from about 0.01 mm to about 50 mm.

8. The mixed lactic acid bacterial culture composition according to claim 1, wherein the additives comprise a cryoprotectant.

9. The mixed lactic acid bacterial culture composition according to claim 1, wherein the composition consists of:
   (1) lactic acid bacteria comprising:
      (a) one or more strains of lactic acid bacteria capable of producing a Class IIa type bacteriocin, wherein at least one of the strains is *Lactobacillus* spp.; and
      (b) one or more strains of lactic acid bacteria capable of producing a Class I type bacteriocin, wherein at least one of the strains of lactic acid bacteria capable of producing a Class I type bacteriocin is selected from the group consisting of *Lactococcus* spp.; and
      (c) optionally, one or more further lactic acid bacterial strains
   (2) water;
   (3) optionally non-lactic acid bacteria.

10. The mixed lactic acid bacterial culture composition according to claim 1, wherein at least one of the one or more strains of lactic acid bacteria capable of producing a Class IIa type bacteriocin is sensitive towards the Class I bacteriocin(s) produced by the one or more strains capable of producing a Class I type bacteriocin.

11. The mixed lactic acid bacterial culture composition according to claim 10, wherein the sensitivity sensitive towards the Class I bacteriocin(s) is defined by, when cultured at its optimal growth temperature during 4 h in 10% reconstituted skimmed milk, a growth in the absence of nisin to a colony forming unit density which is at least 5 times higher than the colony forming unit density that is reached when the same strain is incubated in the presence of 320 IU/ml of nisin under otherwise the same conditions.

* * * * *